(12) United States Patent
Krolewski et al.

(10) Patent No.: US 7,560,244 B2
(45) Date of Patent: Jul. 14, 2009

(54) METHOD OF EVALUATING A SUBJECT FOR RISK OR PREDISPOSITION OF REDUCED RENAL FUNCTION OVER TIME

(75) Inventors: Andrzej S. Krolewski, Needham, MA (US); James H. Warram, Norman, OK (US)

(73) Assignee: Joslin Diabetes Center, Inc., Boston, MA (US)

( * ) Notice: Subject to any disclaimer, the term of this patent is extended or adjusted under 35 U.S.C. 154(b) by 0 days.

(21) Appl. No.: 10/559,014

(22) PCT Filed: Jun. 4, 2004

(86) PCT No.: PCT/US2004/017922

§ 371 (c)(1),
(2), (4) Date: Jun. 19, 2006

(87) PCT Pub. No.: WO2005/002416

PCT Pub. Date: Jan. 13, 2005

(65) Prior Publication Data

US 2006/0240437 A1    Oct. 26, 2006

Related U.S. Application Data

(60) Provisional application No. 60/475,733, filed on Jun. 4, 2003.

(51) Int. Cl.
*G01N 33/50* (2006.01)
*C07K 14/52* (2006.01)

(52) U.S. Cl. .................. 435/7.92; 435/4; 435/7.93; 530/351

(58) Field of Classification Search ................... None
See application file for complete search history.

(56) References Cited

U.S. PATENT DOCUMENTS 7,244,555 B2 *   7/2007   Hu et al. ................ 435/4

FOREIGN PATENT DOCUMENTS

WO    WO 01/11371    2/2001

OTHER PUBLICATIONS

Lemley et al., Kidney International 58: 1228-1237, 2000.*
Nicoletti et al., Diabetogia, 45: 1107-1110, 2002.*
Anders et al., "Chemokines and chemokine receptors are involved in the resolution or progression of renal disease." *Kidney Int.*, 63(2):401-415 (2003).
Banda et al., "Possible relationship of monocyte chemoattractant protein-1 with diabetic nephropathy," *Kidney Int.*, 58:684-690 (2000).
Chiarelli et al., "Circulating Monocyte Chemoattractant Protein-1 and Early Development of Nephropathy in Type 1 Diabetes," *Diabetes Care*, 25(1):1829-1834 (2002).
Cooper et al., "Pathophysiology of Diabetic Nephropathy," *Metabolism*, 47(12 Suppl. 1):3-6 (1998).
Cowley et al., "Increased renal expression of monocyte chemoattractant protein-1 and osteopontin in ADPKD in rats," *Kidney Int.*, 60:2087-2096 (2001).
Esch et al., "Proinflammation: A common denominator or initiator of different pathophysiological disease processes," *Med. Sci. Monit.*, 8(5):HY1-HY9 (2002).
Galteau et al., "Determination of Serum Cystatin C: Biological Variation and Reference Values," *Clin. Chem. Lab. Med.*, 39(9):850-857 (2001).
Golub et al., "Molecular Classification of Cancer: Class Discovery and Class Prediction by Gene Expression Monitoring," *Science*, 286:531-537 (1999).
Han et al., "Role of Monocyte Chemotactic Peptide-1(MCP-1) in Experimental Diabetic Nephropathy," *J. Am. Soc. Nephrol.*, 12:631A, Abstract A3286 (2001).
Harmoinen et al., "Evaluation of plasma cystatin C as a marker for glomerular filtration rate in patients with type 2 diabetes," *Clin. Nephrol.*, 52(6):363-370 (1999).
Katz et al., "An increase in the cell component of the cortical interstitium antedates interstitial fibrosis in type 1 diabetic patients," *Kidney Int.*, 61:2058-2066 (2002).
Kazama et al., "Serum Cystatin C Reliably Detects Renal Dysfunction in Patients with Various Renal Disease," *Nephron*, 91(1):13-20 (2002).
Krolewski et al., "Clinical features and epidemiology of diabetic nephropathy," *Textbook of Diabetes*, Second Edition, Oxford: Blackwell Science Ltd., Chapter 53, pp. 53.1-53.13 (1997).
Krolewski et al., "Magnitude of end-stage renal disease in IDDM: A 35 year follow-up study," *Kidney Int.*, 50:2041-2046 (1996).
Laterza et al., "Cystatin C: An Improved Estimator of Glomerular Filtration Rate?" *Clin. Chem.*, 48(5):699-707 (2002).
Lemley et al., "Evolution of incipient nephropathy in type 2 diabetes mellitus," *Kidney Int.*, 58:1228-1237 (2000).
Maier et al., "Massive chemokine transcription in acute renal failure due to polymicrobial sepsis," *Shock*, 14(2):187-192 (2000).

(Continued)

*Primary Examiner*—Robert Landsman
*Assistant Examiner*—Gyan Chandra
(74) *Attorney, Agent, or Firm*—Fish & Richardson P.C.

(57) ABSTRACT

The invention includes diagnostic, predictive, prognostic and monitoring methods and reagents for loss of renal function, e.g., diabetic nephropathy and end stage renal disease (ESRD).

16 Claims, 3 Drawing Sheets

OTHER PUBLICATIONS

Mauer et al., "Structural-Functional Relationships in Diabetic Nephropathy," *J. Clin. Invest.*, 74:1143-1155 (1984).

Mogensen et al., "Predicting diabetic nephropathy in insulin-dependent patients," *N. Engl. J. Med.*, 311(2):89-93 (1984).

Morii et al., "Association of monocyte chemoattractant protein-1 with renal tubular damage in diabetic nephropathy," *J. Diabetes Complications*, 17:11-15 (2003).

Mussap et al., "Cystatin C is a more sensitive marker than creatinine for the estimation of GFR in type 2 diabetic patients," *Kidney Int.*, 61:1453-1461 (2002).

Newman, "Cystatin C," *Ann. Clin. Biochem.*, 39(Pt. 2):89-104 (2002).

Oberholzer et al., "Cytokine signaling—regulation of the immune response in normal and critically ill states," *Crit. Care Med.*, 28(4 Suppl.):N3-N12 (2000).

Parving et al., "Early detection of patients at risk of developing diabetic nephropathy. A longitudinal study of urinary albumin excretion," *Acta Endocrinol.*, 100:550-555 (1982).

Prodjosudjadi et al., "Production and cytokine-mediated regulation of monocyte chemoattractant protein-1 by human proximal tubular epithelial cells," *Kidney Int.*, 48:1477-1486 (1995).

Ramesh et al., "TNF-$\alpha$ mediates chemokine and cytokine expression and renal injury in cisplatin nephrotoxicity," *J. Clin. Invest.*, 110(6):835-842 (2002).

Saitoh et al., "Detection of Urinary MCP-1 in Patients with Diabetic Nephropathy," *Nephron*, 80(1):99 (1998).

Scott et al., "A Nonlinear Effect of Hyperglycemia and Current Cigarette Smoking Are Major Determinants of the Onset of Microalbuminuria in Type 1 Diabetes," *Diabetes*, 50:2842-2849 (2001).

Taft et al., "Clinical and Histological Correlations of Decline in Renal Function in Diabetic Patients With Proteinuria," *Diabetes*, 43(8):1046-1051 (1994).

Tan et al., "Clinical Usefulness of Cystatin C for the Estimation of Glomerular Filtration Rate in Type 1 Diabetes," *Diabetes Care*, 25(11):2004-2009 (2002).

Tashiro et al., "Urinary Levels of Monocyte Chemoattractant Protein-1 (MCP-1) and Interleukin-8 (IL-8), and Renal Injuries in Patients With Type 2 Diabetic Nephropathy," *J. Clin. Lab. Anal.*, 16:1-4 (2002).

Vesey et al., "Interleukin-1$\beta$ induces human proximal tubule cell injury, $\alpha$-smooth muscle actin expression and fibronectin production," *Kidney Int.*, 62:31-40 (2002).

Viberti et al., "Microalbuminuria as a predictor of clinical nephropathy in insulin-dependent diabetes mellitus," *Lancet*, 1(8287):1430-1432 (1982).

Vielhauer et al., "Obstructive Nephropathy in the Mouse: Progressive Fibrosis Correlates with Tubulointerstitial Chemokine Expression and Accumulation of CC Chemokine Receptor 2- and 5-Positive Leukocytes," *J. Am. Soc. Nephrol.*, 12:1173-1187 (2001).

Wada et al., "Up-regulation of monocyte chemoattractant protein-1 in tubulointerstitial lesions of human diabetic nephropathy," *Kidney Int.*, 58:1492-1499 (2000).

Warram et al., "Effect of Duration of Type I Diabetes on the Prevalence of Stages of Diabetic Nephropathy Defined by Urinary Albumin/Creatinine Ratio," *J. Am. Soc. Nephrol.*, 7(6):930-937 (1996).

Warram et al., "Progression of Microalbuminuria to Proteinuria in Type 1 Diabetes: Nonlinear Relationship With Hyperglycemia," *Diabetes*, 49:94-100 (2000).

White et al., "Podocyte Number in Normotensive Type 1 Diabetic Patients With Albuminuria," *Diabetes*, 51:3083-3089 (2002).

Wilken et al., "Total chemical synthesis and high-resolution crystal structure of the potent anti-HIV protein AOP-RANTES," *Chem. Biol.*, 6(1):43-51 (1999).

Krüger et al., "A Monocyte Chemoattractant Protein-1 (MCP-1) Polymorphism and Outcome After Renal Transplantation," *J. Am. Soc. Nephrol.*, 13:2585-2589 (2002).

Tesch et al., "A monocyte chemoattractant Protein 1-dependent Leukocytic Infllitrates are Responsible for Autoimmune Disease in MRL-$Fas^{lpr}$ Mice," *J. Exp. Med.*, 190(12):1813-1824 (1999).

Wada et al., "Gene Therapy via Blockade of Monocyte Chemoattractant Protein-1 for Renal Fibrosis," *J. Am. Soc. Nephrol.*, 15:940-948 (2004).

\* cited by examiner

METHOD OF EVALUATING A SUBJECT FOR RISK OR PREDISPOSITION OF REDUCED RENAL FUNCTION OVER TIME

The present application claims the benefit of U.S. Ser. No. 60/475,733 filed Jun. 4, 2003.

GOVERNMENT SUPPORT

The work described herein was carried out, at least in part, using funds from the U.S. government under grant number DK41526 awarded by the National Institutes of Health, NIADDK. The government may therefore have certain rights in the invention.

BACKGROUND

Diabetic kidney disease, also known as diabetic nephropathy, is an important cause of excess morbidity and premature mortality in individuals with type 1 diabetes mellitus (T1DM). Approximately 25% to 40% of patients with T1DM ultimately develop diabetic nephropathy. The most serious long-term effect of diabetic nephropathy is kidney failure leading to end stage renal disease (ESRD), a condition in which there is a permanent and almost complete loss of kidney function, with the kidneys functioning at less than 10% of baseline function. Other causes of ESRD include high blood pressure, glomerulonephritis, polycystic kidneys, interstitial disease, obstructive uropathy, systemic lupus erythematosus, and multiple myeloma.

According to prevailing thinking, the development of diabetic nephropathy consists of progression from normoalbuminuria (normal Urinary Albumin Excretion, hereinafter UAE) through three successive clinical stages: 1) microalbuminuria (MA), which is characterized by a small increase in UAE; 2) overt proteinuria, which is characterized by abundant UAE that results in protein over-load of the proximal renal tubules and initiation of renal function loss; and 3) end stage renal disease (ESRD), which requires renal replacement therapy and is coupled with high mortality due to cardiovascular events (Krolewski, et al., *Clinical features and epidemiology of diabetic nephropathy*. In: *Textbook of Diabetes*. Second Ed., eds. Pickup and Williams, pp. 53.1-53-13. Oxford: Blackwell Scientific Publications, 1997).

It has been assumed that, as a result of worsening glomerular damage, a large proportion of patients with MA progress to proteinuria. For example, Mauer et al. have emphasized that expansion of the mesangial extracellular matrix in the glomeruli is the major cause of progression of MA to proteinuria and consequently of renal function loss (Mauer et al., *J Clin Invest* 74:1143-55, 1984). Recently some evidence and many speculations have been put forward emphasizing importance of loss of podocytes (epithelial cells covering the glomeruli) as a mechanism for the development of proteinuria (Lemley et al,. *Kidney Int* 58:1228-1237, 2000; White et al., *Diabetes* 51:3083-3089, 2002). It is believed that after patients with T1DM progress to proteinuria, tubular damage begins and leads to tubulointerstitial injury and subsequent fibrosis and loss of renal function (Taft et al., *Diabetes* 43:1046-51, 1994; Katz et al., *Kidney Int* 61:2056-66, 2002).

SUMMARY OF THE INVENTION

The invention is based, in part, on the inventors' discovery that declining renal function (e.g., in patients at risk for serious renal disease, e.g., diabetic patients) can be detected before an overt sign or symptom of renal disease (such as proteinuria or decreased glomerular filtration rate (GFR)) is present. The inventors have found that detection of a particular profile of chemokines and/or cytokines or other proteins (e.g., levels of one or more of MCP-1, IL-8, IP-10, MIF, FGF-2, PDGF-AA, uPA, uPAR, and fibronectin) in a subject without an overt sign or symptom of renal disease (e.g., in a subject with normoalbuminuria or microalbuminuria) correlates with the presence of a process that can lead to a decline in renal function (e.g., a decline in glomerular filtration rate (GFR)). Unlike currently available tools that provide static measures of decreased renal function, such a profile can predict the decline of renal function early in the destructive process while renal function (e.g., as evaluated by art recognized measures for renal function, such as GFR) is within the normal range. It is an advantage of the claimed methods that they allow for predicting a loss of renal function in a subject before an overt sign or symptom of loss of renal function is present. Thus, the invention features methods and compositions relating to early diagnosis, prognosis and/or monitoring of loss of renal function.

Accordingly, in one aspect, the invention features a method of evaluating a subject, e.g., determining risk, predisposition, or presence of a process reducing renal function (e.g., GFR) in the subject over time, e.g., a clinically significant rate of loss of renal function. Such a process can eventually lead to a severe stage of renal disease (e.g., end stage renal disease), in a subject, e.g., a human. The method includes identifying, selecting, or diagnosing a subject having normoalbuminuria or microalbuminuria; and evaluating the gene, expression, level or activity of one or more of: MCP-1, IL-8, IP-10, MIF, FGF-2, PDGF-AA, uPA, uPAR and fibronectin in the subject, e.g., in a urine sample. In a preferred embodiment, at least one of the genes or proteins evaluated is a chemokine gene or protein. An aberrant gene, expression, level or activity can be correlated with risk, predisposition, or presence of a process that can reduce renal function (e.g., GFR) over time. The subject is preferably a diabetic subject, e.g., a diabetic human.

In a preferred embodiment, the subject has normal kidney function as defined by a clinical measure, e.g., GFR, urine protein level, blood creatinine level, urine creatinine level, creatinine clearance, and/or blood urea nitrogen.

In a preferred embodiment, an elevated level, activity or expression of one or more of: MCP-1, IL-8, IP-10, MIF, FGF-2, PDGF-AA, uPA, uPAR and fibronectin is correlated with risk for loss of renal function over time.

In a preferred embodiment, an elevated level, activity or expression of one or more of: MCP-1, IL-8, IP-10, MIF, FGF-2, PDGF-AA, uPA, uPAR and fibronectin is correlated with early or accelerated loss of renal function. "Early or accelerated loss of renal function" means that renal function is lost, e.g., at a clinically significant rate, before, during, or soon after, the onset of microalbuminuria but before development of proteinuria.

The correlation can be in the form of informational, diagnostic, prognostic, marketing or instructional material (e.g., print or computer readable material) identifying the subject having an aberrant gene, expression, level or activity of one or more of: MCP-1, IL-8, IP-10, MIF, FGF-2, PDGF-AA, uPA, uPAR and fibronectin as being at risk for, or predisposed to, severe renal disease or loss (e.g., rapid loss) of renal function (e.g., GFR), e.g., a clinically significant rate of loss of renal function. In one embodiment, the method includes correlating a value for the evaluated parameter (e.g., expression, level or activity) with risk or rate of loss of renal function (e.g., GFR), e.g., generating a dataset correlating a value for the evaluated parameter with risk or rate of loss of renal function.

The method can include providing a record, e.g., a print or computer readable material, e.g., an informational, diagnostic, or instructional material, e.g., to the subject, a health care provider, or an insurance company, identifying the abnormal or gene, expression, level or activity as a risk or diagnostic factor for early or accelerated loss of renal function.

In a preferred embodiment, the method (as well as other related methods described herein) can be performed in an array, e.g., an array that detects the gene, expression, level or activity of two or more of MCP-1, IL-8, IP-10, MIF, FGF-2, PDGF-AA, uPA, uPAR and fibronectin. In a particularly preferred embodiment, at least one of the genes or proteins detected is a chemokine gene or protein.

In a preferred embodiment, the level of MCP-1 is correlated with risk, predisposition, or presence of a process reducing renal function (e.g., GFR) over time if it is at least 20% higher, preferably at least 30% higher, more preferably at least 50% higher or more (e.g., 60, 70, 80, 90% higher) than a reference value, e.g., a control or baseline value. In some embodiments, the level of MCP-1 is correlated with risk, predisposition, or presence of a process reducing renal function (e.g., GFR) over time if it is qualitatively higher than a reference value, e.g., a control or baseline value. In some embodiments, the level of MCP-1 can be more than twice the reference value.

In a preferred embodiment, the level of IL-8 is correlated with risk, predisposition, or presence of a process reducing renal function (e.g., GFR) over time if it is at least 20% higher, preferably at least 30% higher, more preferably at least 50% higher or more (e.g., 60, 70, 80, 90% higher) than a reference value, e.g., a control or baseline value. In some embodiments, the level of IL-8 is correlated with risk, predisposition, or presence of a process reducing renal function (e.g., GFR) over time if it is qualitatively higher than a reference value, e.g., a control or baseline value. In some embodiments, the level of IL-8 can be more than twice the reference value.

In a preferred embodiment, the level of IP-10 is correlated with risk, predisposition, or presence of a process reducing renal function (e.g., GFR) over time if it is at least 20% higher, preferably at least 30% higher, more preferably at least 50% higher or more (e.g., 60, 70, 80, 90% higher) than a reference value, e.g., a control or baseline value. In some embodiments, the level of IP-10 is correlated with risk, predisposition, or presence of a process reducing renal function (e.g., GFR) over time if it is qualitatively higher than a reference value, e.g., a control or baseline value. In some embodiments, the level of IP-10 can be more than twice the reference value.

In a preferred embodiment, the level of MIF is correlated with risk, predisposition, or presence of a process reducing renal function (e.g., GFR) over time if it is at least 20% higher, preferably at least 30% higher, more preferably at least 50% higher or more (e.g., 60, 70, 80, 90% higher) than a reference value, e.g., a control or baseline value. In some embodiments, the level of MIF is correlated with risk, predisposition, or presence of a process reducing renal function (e.g., GFR) over time if it is qualitatively higher than a reference value, e.g., a control or baseline value. In some embodiments, the level of MIF can be more than twice the reference value.

In one embodiment, the evaluation includes contacting a biological sample of the subject, preferably a urine sample, with an agent that detects MCP-1, IL-8, IP-10, MIF, FGF-2, PDGF-AA, uPA, uPAR and/or fibronectin. The agent, e.g., an antibody or nucleic acid probe, can be immobilized on a solid phase, e.g., on a microtiter well, tube, dipstick or other test device. In a preferred embodiment, the gene, expression, presence, level, or activity is detected using a dipstick or other test device format assay.

In preferred embodiment, the subject is at risk for, or has, one or more of: diabetes (e.g., type 1 diabetes mellitus (T1DM) or type 2 diabetes). In other embodiments, the subject is at risk for, or has, one or more of: hypertension, glomerulonephritis, polycystic kidneys, interstitial disease, obstructive uropathy, systemic lupus erythematosus, or multiple myeloma.

In a preferred embodiment, the level or activity is evaluated in a urinary sample of the subject.

In a preferred embodiment, the evaluating step comprises performing one or more of: enzyme-linked immunoassay, radioimmunoassay, immunoblot assay, in situ hybridization, Northern blot analysis, Western blot analysis, and Luminex™×MAP™ detection.

In a preferred embodiment, the method also includes evaluating albumin levels, e.g., in the urine of the subject. Such evaluation can be performed by known techniques, e.g., by immunoassay, e.g., radioimmunoassay, immunonephelometry or immunoturbidimetry.

In one embodiment, the method includes: identifying a subject at risk for, or having, diabetes, wherein the subject has normoalbuminuria or microalbuminuria, and evaluating the level or activity of one or more of: MCP-1, IL-8, IP-10, MIF, FGF-2, PDGF-AA, uPA, uPAR and fibronectin in a urinary sample of the subject, wherein an elevated level or activity is correlated with risk, predisposition, or presence of a process reducing renal function (e.g., GFR) over time. In a preferred embodiment, at least one of the levels or activities evaluated is a chemokine level or activity.

In a preferred embodiment, the method includes treating the subject for the renal disorder.

In a preferred embodiment, the subject is further evaluated for one or more of the following parameters: (1) albumin levels; (2) insulin level; (3) glucose levels; (4) GFR; (5) serum cystatin C; (6) blood creatinine; (7) urine creatine; (8) creatinine clearance.

In a preferred embodiment, the evaluation is used to choose a course of treatment. For example, if the subject is determined to be at risk for loss of renal function or renal disease, the treatment can include dietary restrictions.

In one embodiment, the evaluation is performed by the subject. In another embodiment, the evaluation is performed by a health care provider. In yet another embodiment, the evaluation is performed by a third party.

In another aspect, the invention features a method of evaluating a treatment for renal disease, e.g., diabetic nephropathy or end stage renal disease. The method includes administering a treatment to a subject at risk for, or having, renal disease; and evaluating the expression, level or activity of one or more of: MCP-1, IL-8, IP-10, MIF, FGF-2, PDGF-AA, uPA, uPAR and fibronectin in a biological sample of the subject, e.g., a urine sample. In a preferred embodiment, at least one of the expression, levels, or activities evaluated is the expression, level, or activity of a chemokine. A decrease in expression, level or activity can indicate effectiveness of the treatment.

In another aspect, the invention features a kit for detecting, predicting, diagnosing and/or monitoring renal disease or risk, predisposition, or presence of a process reducing renal function (e.g., GFR) over time. The kit includes an agent capable of detecting one or more of: IL-8, IP-10, MCP-1, MIF, FGF-2, PDGF-AA, uPA, uPAR and/or fibronectin, in a biological sample of a subject, e.g., a human; and instructions for using the agent to evaluate risk, predisposition, or prognosis for renal disease in a subject. In a preferred embodiment, the kit includes an agent capable of detecting at least one chemokine.

In one embodiment, the kit includes instructions to use (e.g., to contact the agent) with a sample from a subject (preferably a human) having microalbuminuria. In another embodiment, the kit includes instructions for use with a sample from a subject having normoalbuminuria. In yet another embodiment, the kit includes instructions for use with a sample from a subject having diabetes, e.g., T1DM or type 2 diabetes. In other embodiments, the kit includes instructions for use with a sample from a subject having hypertension, glomerulonephritis, polycystic kidneys, interstitial disease, obstructive uropathy, systemic lupus erythematosus, and multiple myeloma.

In a preferred embodiment, the instructions comprise instructions for use by or for a subject who has normal kidney function as defined by a clinical measure, e.g., GFR, urine protein level, blood creatinine level, urine creatinine level, creatinine clearance, and/or blood urea nitrogen.

In one embodiment, the kit includes an assay for albumin levels.

In a preferred embodiment, the instructions comprise directions to contact the agent with a urine sample of the subject.

In a preferred embodiment, the agent is attached to a solid substrate, e.g., a microtiter well, a tube, a sheet (e.g., a nitrocellulose sheet), a dipstick or other test device. Preferably, the kit includes a dipstick or other test device.

In a preferred embodiment, the agent is an antibody. The antibody can be attached to a detectable label, e.g., an enzyme, a calorimetric reagent, a fluorescent substance, or a radioactive isotope.

In a preferred embodiment, the kit includes a positive and/or a negative control. The kit can also include a densitometer, or electrochemical strip.

In one embodiment, the instructions include instructions for the subject to perform the evaluation. In another embodiment, the instructions include instructions for a health care provider to perform the evaluation. In yet another embodiment, the instructions include instructions for a third person to perform the evaluation. For example, in one embodiment, the instructions include instructions to contact the agent, e.g., a solid substrate to which the agent is attached, with the subject's urine, and provide (e.g., mail) the contacted substrate to a third party to perform the evaluation.

In another aspect, the invention features a method of providing a health care service or product, e.g., a diagnostic test. The method includes: supplying a test substrate (e.g., a tube, a strip, a dipstick, other test device, or a well) to which is attached an agent capable of detecting one or more of: IL-8, IP-10, MCP-1, MIF, FGF-2, PDGF-AA, uPA, uPAR and/or fibronectin; and supplying instructions to contact the test substrate with a subject's urine. The method optionally includes supplying instructions for reading, evaluating or interpreting the contacted substrate, e.g., to evaluate risk, predisposition, or presence of a process reducing renal function (e.g., GFR) over time in a subject. In a preferred embodiment, the instructions comprise instructions to use for a subject who has normal kidney function as defined by a clinical measure, e.g., GFR, urine protein level, blood creatinine level, urine creatinine level, creatinine clearance, and/or blood urea nitrogen.

In one embodiment, the instructions include instructions to use (e.g., to contact the agent) with a urine sample from a subject having microalbuminuria. In another embodiment, the instructions include instructions for use with a urine sample from a subject having normoalbuminuria. In yet another embodiment, the instructions include instructions for use with a urine sample from a subject having diabetes, e.g., T1DM or type 2 diabetes. In other embodiments, the instructions include instructions for use with a urine sample from a subject having hypertension, glomerulonephritis, polycystic kidneys, interstitial disease, obstructive uropathy, systemic lupus erythematosus, and multiple myeloma.

In one embodiment, the instructions for evaluating (e.g., reading or interpreting) the contacted substrate include instructions for the subject to perform the evaluation. In another embodiment, the instructions for evaluating (e.g., reading or interpreting) the contacted substrate include instructions for a health care provider to perform the evaluation. In yet another embodiment, the instructions for evaluating (e.g., reading or interpreting) the contacted substrate include instructions for a third person to perform the evaluation. For example, in one embodiment, the instructions include instructions to contact the substrate with the subject's urine, and provide (e.g., mail) the contacted substrate to a third party to perform the evaluation.

In a preferred embodiment, the agent is an antibody. The antibody can be attached to a detectable label, e.g., an enzyme, a colorimetric reagent, a fluorescent substance, or a radioactive isotope.

In a preferred embodiment, the test substrate includes a positive and/or a negative control.

In another aspect, the invention features a method of treating a subject. The method includes identifying a subject having or at risk for early loss of renal function; and modulating MCP-1, IL-8, IP-10, MIF, FGF-2, PDGF-AA, uPA, uPAR and/or fibronectin expression, levels or activity in the subject. In a preferred embodiment, the method includes modulating at least one chemokine.

In a preferred embodiment, the subject has microalbuminuria. In another preferred embodiment, the subject has diabetes. In another preferred embodiment, the subject has hypertension, glomerulonephritis, polycystic kidneys, interstitial disease, obstructive uropathy, systemic lupus erythematosus, or multiple myeloma.

In a preferred embodiment, modulating MCP-1, IL-8, IP-10, MIF, FGF-2, PDGF-AA, uPA, uPAR and/or fibronectin comprises administering an agent that modulates, e.g., inhibits IL-8, IP-10, MCP-1, MIF, FGF-2, PDGF-AA, uPA, uPAR and/or fibronectin signaling. In a particularly preferred embodiment, the agent modulates at least one chemokine. The agent can be an antibody, small molecule, or a modified, e.g., chemically modified or derivatized protein.

In a preferred embodiment, the agent inhibits the expression, levels, or activity of IL-8, IP-10, MCP-1, MIF, FGF-2, PDGF-AA, uPA, or fibronectin (or their receptors, e.g., IL8RA, IL8RB, CXCR3 (IP-10 receptor), CCR2B (MCP-1 receptor), CD74 (MIF receptor), FGFR1, FGFR2, FGFR3, PDGFRα, or uPAR), to thereby increase renal function. An agent that decreases the expression, levels, or activity of IL-8, IP-10, MCP-1, MIF, FGF-2, PDGF-AA, uPA, or fibronectin (or their receptors, e.g., IL8RA, IL8RB, CXCR3, CCR2B, CD74, FGFR1, FGFR2, FGFR3, PDGFRα, or uPAR) can be one or more of: an IL-8, IP-10, MCP-1, MIF, FGF-2, PDGF-AA, uPA, fibronectin, IL8RA, IL8RB, CXCR3, CCR2B, CD74, FGFR1, FGFR2, FGFR3, PDGFRα, or uPAR binding protein, e.g., a soluble IL-8, IP-10, MCP-1, MIF, FGF-2, PDGF-AA uPA, fibronectin, IL8RA, IL8RB, CXCR3, CCR2B, CD74, FGFR1, FGFR2, FGFR3, PDGFRα, or uPAR binding protein that binds and inhibits protein activity, e.g., an IL-8, IP-10, MCP-1, MIF, FGF-2, PDGF-AA, uPA, fibronectin, IL8RA, IL8RB, CXCR3, CCR2B, CD74, FGFR1, FGFR2, FGFR3, PDGFRα, or uPAR activity; an antibody or antigen binding fragment thereof that specifically binds to an IL-8, IP-10, MCP-1, MIF, FGF-2, PDGF-AA, uPA, fibronectin, IL8RA, IL8RB, CXCR3, CCR2B, CD74, FGFR1, FGFR2, FGFR3, PDGFRα, or uPAR protein, e.g., an antibody that disrupts the ability of a protein described herein to bind to another protein, e.g., its receptor; a mutated inactive IL-8, IP-10, MCP-1, MIF, FGF-2, PDGF-AA, uPA, fibronectin, IL8RA, IL8RB, CXCR3, CCR2B, CD74, FGFR1, FGFR2, FGFR3, PDGFRα, or uPAR, or fragment thereof that, e.g., lacks an activation domain or a binding domain; an IL-8, IP-10, MCP-1, MIF, FGF-2, PDGF-AA, uPA, fibronectin, IL8RA, IL8RB, CXCR3, CCR2B, CD74, FGFR1, FGFR2, FGFR3, PDGFRα, or uPAR nucleic acid molecule that can bind to a cellular IL-8, IP-10, MCP-1, MIF, FGF-2, PDGF-AA, uPA, fibronectin, IL8RA, IL8RB, CXCR3, CCR2B, CD74, FGFR1, FGFR2, FGFR3, PDGFRα, or uPAR nucleic acid sequence, e.g., mRNA, and inhibit expression of the protein, e.g., an antisense molecule, siRNA or ribozyme; an agent that decreases IL-8, IP-10, MCP-1, MIF, FGF-2, PDGF-AA, uPA, fibronectin, IL8RA, IL8RB, CXCR3, CCR2B, CD74, FGFR1, FGFR2, FGFR3, PDGFRα, or uPAR gene expression, e.g., a small molecule that binds the promoter of IL-8, IP-10, MCP-1, MIF, FGF-2, PDGF-AA uPA, fibronectin, IL8RA, IL8RB, CXCR3, CCR2B, CD74, FGFR1, FGFR2, FGFR3, PDGFRα, or uPAR and decreases gene expression. In another preferred embodiment, IL-8, IP-10, MCP-1, MIF, FGF-2, PDGF-AA, uPA, fibronectin, IL8RA, IL8RB, CXCR3, CCR2B, CD74, FGFR1, FGFR2, FGFR3, PDGFRα, or uPAR is inhibited by decreasing the level of expression of an endogenous IL-8, IP-10, MCP-1, MIF, FGF-2, PDGF-AA, uPA, fibronectin, IL8RA, IL8RB, CXCR3, CCR2B, CD74, FGFR1, FGFR2, FGFR3, PDGFRα, or uPAR gene, e.g., by decreasing transcription of the gene. In a preferred embodiment, transcription of the IL-8, IP-10, MCP-1, MIF, FGF-2, PDGF-AA, uPA, fibronectin, IL8RA, IL8RB, CXCR3, CCR2B, CD74, FGFR1, FGFR2, FGFR3, PDGFRα, or uPAR gene can be decreased by: altering the regulatory sequences of the endogenous IL-8, IP-10, MCP-1, MIF, FGF-2, PDGF-AA, uPA, fibronectin, IL8RA, IL8RB, CXCR3, CCR2B, CD74, FGFR1, FGFR2, FGFR3, PDGFRα, or uPAR gene, e.g., by the addition of a negative regulatory sequence (such as a DNA-biding site for a transcriptional repressor), or by the removal of a positive regulatory sequence (such as an enhancer or a DNA-binding site for a transcriptional activator).

Antagonists of IL-8 signaling are known and can be used in vivo (see, e.g., Li et al. Biochem Biophys Res Commun 2002 May 10;293(3):939-44; Podolin et al. J Immunol 2002 Dec. 1;169(11):6435-44, describing a potent and selective nonpeptide antagonist of an IL-8 receptor; Sanz et al., J Immunol 1995 Feb. 1;154(3):1364-73, describing anti-human IL-8 mAb DM/C7). Antagonists of MCP-1 are also known. See, e.g., Gong et al. *J. Exp. Med.* 181: 631-640, describing the peptide analog antagonist MCP-1(9-76); Bruno et al. *Int J Immunopathol Pharmacol* 2002 15(2):113-118, describing cetirizine as an MCP-1 antagonist in vivo; Rhodes et al. *FEBS Lett* 2001 506(2):85-90, describing antagonist RNA aptamers to MCP-1.

In a preferred embodiment, the method includes evaluating the subject for renal function or risk, predisposition, or presence of a process reducing renal function (e.g., GFR) over time, e.g., using a monitoring method described herein, e.g., wherein levels of one or more of MCP-1, IL-8, IP-10, MIF, FGF-2, PDGF-AA, uPA, uPAR, and/or fibronectin is detected. In a particularly preferred embodiment, the method includes detecting the level of at least one chemokine. The method can also include evaluating the subject for albumin levels in the urine.

In a preferred embodiment, the administration of the agent can be initiated, e.g., (a) when the subject begins to show signs of early loss of renal function, as evidenced by microalbuminuria, or an increase of more than 5, 10, 20, or 30% in a diagnostic method described herein compared to a reference value, e.g., control, e.g., a non-disease state control; (b) when a renal disorder, e.g., early loss of renal function, is diagnosed; (c) before, during or after a treatment for an a renal disorder, is begun or begins to exert its effects; or (d) generally, as is needed to maintain health, e.g., kidney health, e.g., throughout the natural aging process. The period over which the agent is administered (or the period over which clinically effective levels are maintained in the subject) can be long term, e.g., for six months or more or a year or more, or short term, e.g., for less than a year, six months, one month, two weeks or less.

In a preferred embodiment, IL-8, IP-10, MCP-1, MIF, FGF-2, PDGF-AA, uPA, or fibronectin (or their receptors, e.g., IL8RA, IL8RB, CXCR3 (IP-10 receptor), CCR2B (MCP-1 receptor), CD74, FGFR1, FGFR2, FGFR3, PDGFRα, or uPAR) activity, levels or expression is modulated, e.g., decreased, in the kidney, e.g., in tubular or glomerular cells of the kidney.

In a preferred embodiment, a pharmaceutical composition including one or more of the agents described herein is administered in a pharmaceutically effective dose.

In a preferred embodiment, the subject is a human.

In a preferred embodiment, the chemically modified protein is a modified derivative that acts as a receptor antagonist. Methods of making such modified derivatives are exemplified, e.g., in Proudfoot, et al., *J. Biol. Chem.* 271:2599-2603, 1996; Simmons et al., *Science* 276:276-279, 1997; and U.S. Published Application 20030017979.

In another preferred embodiment, the antagonist is an antagonist of one or more of IL8RA, IL8RB, CXCR3, CCR2B, CD74, FGFR1, FGFR2, FGFR3, PDGFRα, and uPAR.

In another aspect, the invention features a method of evaluating an agent, e.g., screening for an agent, that modulates renal function. The method includes (a) providing a test agent, (b) determining if the agent interacts with one or more of: MCP-1, IL-8, IP-10, MIF, FGF-2, PDGF-AA, uPA, uPAR, or fibronectin, e.g., binds to and/or modulates the levels, expression, or activity of one or more of: MCP-1, IL-8, IP-10, MIF, FGF-2, PDGF-AA, uPA, uPAR, or fibronectin, and (c) correlating the ability of a test agent to modulate MCP-1, IL-8, IP-10, MIF, FGF-2, PDGF-AA, uPA, uPAR, or fibronectin with the ability to modulate renal function. Correlating means identifying a test agent that modulates MCP-1, IL-8, IP-10, MIF, FGF-2, PDGF-AA, uPA, uPAR, or fibronectin as an agent capable of modulating renal function, e.g., providing a record, e.g., a print or computer readable record, such as a laboratory record or dataset, identifying a test agent that modulates MCP-1, IL-8, IP-10, MIF, FGF-2, PDGF-AA, uPA, uPAR, or fibronectin as an agent capable of modulating renal function. The record can include other information, such as a specific test agent identifier, a date, an operator of the method, or information about the source, structure, method of purification or biological activity of the test agent. The record or information derived from the record can be used, e.g., to identify the test agent as a compound or lead compound for pharmaceutical or therapeutic use. Agents, e.g., compounds, identified by this method can be used, e.g., in the treatment of renal disease, e.g., diabetic nephropathy or ESRD.

In one embodiment, the method includes: providing an MCP-1, IL-8, IP-10, MIF, FGF-2, PDGF-AA, uPA, or fibronectin, or a receptor for MCP-1, IL-8, IP-10, MIF, FGF-2, PDGF-AA, uPA, or fibronectin (such as IL8RA, IL8RB, CXCR3, CCR2B, CD74, FGFR1, FGFR2, FGFR3, PDGFRα, or uPAR), e.g., MCP-1, IL 8, IP-10, MIF, FGF-2, PDGF-AA, uPA, fibronectin, IL8RA, IL8RB, CXCR3, CCR2B, CD74, FGFR1, FGFR2, FGFR3, PDGFRα, uPAR protein or nucleic acid or a functional fragment thereof; contacting the MCP-1, IL-8, IP-10, MIF, FGF-2, PDGF-AA, uPA, fibronectin, IL8RA, IL8RB, CXCR3, CCR2B, CD74, FGFR1, FGFR2, FGFR3, PDGFRα, or uPAR protein or nucleic acid with a test agent, and determining if the test compound interacts with, e.g., binds, the protein or nucleic acid.

In one embodiment, the test agent binds to the MCP-1, IL-8, IP-10, MIF, FGF-2, PDGF-AA, uPA, fibronectin, IL8RA, IL8RB, CXCR3, CCR2B, CD74, FGFR1, FGFR2, FGFR3, PDGFRα, or uPAR protein and modulates activity, e.g., chemokine and/or cytokine signaling, protease activity, and/or substrate binding. For example, the test agent binds to the MCP-1, IL-8, IP-10, MIF, FGF-2, PDGF-AA, uPA, fibronectin, IL8RA, IL8RB, CXCR3, CCR2B, CD74, FGFR1, FGFR2, FGFR3, PDGFRα, or uPAR protein and facilitates or inhibits activity, e.g., chemokine and/or cytokine signaling, protease activity, and/or substrate binding activity. Methods for assaying chemokine activity, cytokine activity, protease activity or substrate binding activity are art-recognized.

In a preferred embodiment, the test compound is one or more of: a protein or peptide; an antibody; a small molecule; a nucleotide sequence. For example, the agent can be an agent identified through a library screen described herein.

In a preferred embodiment, the contacting step is performed in vitro.

In another preferred embodiment, the contacting step is performed in vivo.

In a preferred embodiment, the method further includes administering the test compound to an experimental animal, e.g., an animal model for renal disease, e.g., diabetic nephropathy or ESRD.

In another embodiment, the method includes: providing a test cell, tissue, or subject; administering a test agent to the cell, tissue, or subject; and determining whether the test agent modulates MCP-1, IL-8, IP-10, MIF, FGF-2, PDGF-AA, uPA, uPAR, and/or fibronectin activity, e.g., modulates MCP-1, IL-8, IP-10, MIF, FGF-2, PDGF-AA, uPA, fibronectin, IL8RA, IL8RB, CXCR3, CCR2B, CD74, FGFR1, FGFR2, FGFR3, PDGFRα, and/or uPAR expression, level or activity in the cell, tissue, or subject. An agent that is found to decrease MCP-1, IL-8, IP-10, MIF, FGF-2, PDGF-AA, uPA, uPAR and/or fibronectin activity in the cell, tissue, or subject is identified as an agent that can modulate renal function.

In a preferred embodiment, the cell is a kidney cell, e.g., a tubular cell or glomerular cell.

In a preferred embodiment, the method includes (a) providing a cell-free expression system, cell, tissue, or animal having a transgene which includes a nucleic acid that encodes a reporter molecule functionally linked to the control region, e.g., a promoter, of a gene encoding a MCP-1, IL-8, IP-10, MIF, FGF-2, PDGF-AA, uPA, fibronectin, IL8RA, IL8RB, CXCR3, CCR2B, CD74, FGFR1, FGFR2, FGFR3, PDGFRα, or uPAR protein; (b) contacting the cell-free expression system, cell, tissue, or animal with a test agent; and (c) evaluating a signal produced by the reporter molecule. A test agent that causes the modulation of reporter molecule expression, compared to a reference, e.g., a negative control, is identified as an agent that can modulate renal function. Preferred agents decrease expression, levels or activity of MCP-1, IL-8, IP-10, MIF, FGF-2, PDGF-AA, uPA, fibronectin, IL8RA, IL8RB, CXCR3, CCR2B, CD74, FGFR1, FGFR2, FGFR3, PDGFRα, or uPAR.

In a preferred embodiment, the reporter molecule is any of: green fluorescent protein (GFP); enhanced GFP (EGFP); luciferase; chloramphenicol acetyl transferase (CAT); β-galactosidase; β-lactamase; or secreted placental alkaline phosphatase. Other reporter molecules, e.g., other enzymes whose function can be detected by appropriate chromogenic or fluorogenic substrates, are known to those skilled in the art.

In a preferred embodiment, the agent is further tested in a cell-based and/or animal based model e.g., a cell based or animal model described herein.

In another aspect, the invention features a method of making a diagnostic device. The method includes supplying a substrate, e.g., a dipstick or other test device, well, tube, or strip; and adhering an agent that detects one or more of MCP-1, IL-8, IP-10, MIF, FGF-2, PDGF-AA, uPA, uPAR, and fibronectin (e.g., an anti-MCP-1, -IL-8, -IP-10, -MIF, -FGF-2, -PDGF-AA, -uPA, -uPAR, or -fibronectin antibody) to the substrate. In a preferred embodiment, the method includes adhering an agent that detects at least one chemokine. In a preferred embodiment, the agent is applied by spraying, deposition of a liquid, or printing.

In another aspect, the invention features a computer readable record encoded with (a) a subject identifier, e.g., a patient identifier, (b) one or more results from an evaluation of the subject, e.g., a diagnostic evaluation described herein, e.g., the level of expression, level or activity of MCP-1, IL-8, IP-10, MIF, FGF-2, PDGF-AA, uPA, uPAR, and/or fibronectin, in the subject, and optionally (c) a value for or related to a disease state, e.g., a value correlated with disease status or risk with regard to renal function, e.g., early loss of renal function. In one embodiment, the invention features a computer medium having a plurality of digitally encoded data records. Each data record includes a value representing the level of expression, level or activity of a MCP-1, IL-8, IP-10, MIF, FGF-2, PDGF-AA, uPA, uPAR, or fibronectin, in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression, level or activity of genes other than MCP-1, IL-8, IP-10, MIF, FGF-2, PDGF-AA, uPA, fibronectin, IL8RA, IL8RB, CXCR3, CCR2B, CD74, FGFR1, FGFR2, FGFR3, PDGFRα, or uPAR (e.g., other genes associated with renal function, or other genes on an array). The data record can be structured as a table, e.g., a table that is part of a database such as a relational database (e.g., a SQL database of the Oracle or Sybase database environments). The invention also includes a method of communicating information about a subject, e.g., by transmitting information, e.g., transmitting a computer readable record described herein, e.g., over a computer network.

In another aspect, the invention features a method of providing information, e.g., for making a decision with regard to the treatment of a subject having, or at risk for, a renal disease described herein. The method includes (a) evaluating the expression, level or activity of MCP-1, IL-8, IP-10, MIF, FGF-2, PDGF-AA, uPA, uPAR, and/or fibronectin; optionally (b) providing a value for the expression, level or activity of MCP-1, IL-8, IP-10, MIF, FGF-2, PDGF-AA, uPA, uPAR, and/or fibronectin; optionally (c) comparing the provided value with a reference value, e.g., a control or non-disease state reference or a disease state reference; and optionally (d) based on, e.g., the relationship of the provided value to the reference value, supplying information, e.g., information for making a decision on or related to the treatment of the subject.

In a preferred embodiment, the provided value relates to an activity described herein, e.g., to a chemokine or cytokine signaling activity, protease activity, and/or substrate binding activity.

In a preferred embodiment, the decision is whether to administer a preselected treatment.

In a preferred embodiment, the decision is whether a party, e.g., an insurance company, HMO, or other entity, will pay for all or part of a preselected treatment.

Also featured is a method of evaluating a sample. The method includes providing a sample, e.g., from the subject, and determining a gene expression profile of the sample, wherein the profile includes a value representing the level of expression of MCP-1, IL-8, IP-10, MIF, FGF-2, PDGF-AA, uPA, fibronectin, IL8RA, IL8RB, CXCR3, CCR2B, CD74, FGFR1, FGFR2, FGFR3, PDGFRα, or uPAR. The method can further include comparing the value or the profile (i.e., multiple values) to a reference value or reference profile. The gene expression profile of the sample can be obtained by methods known in the art (e.g., by providing a nucleic acid from the sample and contacting the nucleic acid to an array). The method can be used to diagnose or predict a renal disease, e.g., a renal disease described herein, in a subject wherein misexpression of MCP-1, IL-8, IP-10, MIF, FGF-2, PDGF-AA, uPA, fibronectin, IL8RA, IL8RB, CXCR3, CCR2B, CD74, FGFR1, FGFR2, FGFR3, PDGFRα, and/or uPAR, e.g., an increase in activity, is an indication that the subject has a risk, predisposition, or presence of a process reducing renal function (e.g., GFR) over time. The method can be used to monitor a treatment for renal disease in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) Science 286:531).

In another aspect, the invention features, a method of evaluating a subject. The method includes: a) obtaining a sample from a subject, e.g., from a caregiver, e.g., a caregiver who obtains the sample from the subject; and b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of expression of MCP-1, IL-8, IP-10, MIF, FGF-2, PDGF-AA, uPA, fibronectin, IL8RA, IL8RB, CXCR3, CCR2B, CD74, FGFR1, FGFR2, FGFR3, PDGFRα, uPAR, or another protein described herein, e.g., a cytokine, cytokine receptor, chemokine or chemokine receptor described herein. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of expression of MCP-1, IL-8, IP-10, MIF, FGF-2, PDGF-AA, uPA, fibronectin, IL8RA, IL8RB, CXCR3, CCR2B, CD74, FGFR1, FGFR2, FGFR3, PDGFRα, and/or uPAR.

As used herein, "treatment" or "treating a subject" is defined as the application or administration of a therapeutic agent to a patient, or application or administration of a therapeutic agent to an isolated tissue or cell line from a patient, e.g., a kidney cell or tissue, who has a disease, a symptom of disease or a predisposition toward a disease, e.g., ESRD. Treatment can slow, cure, heal, alleviate, relieve, alter, remedy, ameliorate, improve or affect the disease, a symptom of the disease or the predisposition toward disease, e.g., by at least 10%.

As used herein, to ability of a first molecule to "interact" with a second molecule refers to the ability of the first molecule to act upon the structure and/or activity of the second molecule, either directly or indirectly. For example, a first molecule can interact with a second by (a) directly binding, e.g., specifically binding, the second molecule, e.g., transiently or stably binding the second molecule; (b) modifying the second molecule, e.g., by cleaving a bond, e.g., a covalent bond, in the second molecule, or adding or removing a chemical group to or from the second molecule, e.g., adding or removing a phosphate group or carbohydrate group; (c) modulating an enzyme that modifies the second molecule, e.g., inhibiting or activating a kinase or phosphatase that normally modifies the second molecule; (d) affecting expression of the second molecule, e.g., by binding, activating, or inhibiting a control region of a gene encoding the second molecule, or binding, activating, or inhibiting a transcription factor that associates with the gene encoding the second molecule; or (e) affecting the stability of an mRNA encoding the second molecule, e.g., by inhibiting mRNAse activity against the mRNA encoding the second molecule or by degrading the mRNA encoding the second molecule.

As used herein, "early or accelerated loss of renal function" means a loss or decline in renal function before, during, or soon after, the onset of microalbuminuria but before development of proteinuria. For example, renal function is lost at a clinically significant rate before, during, or soon after, the onset of microalbuminuria but before development of proteinuria.

As used herein, "microalbuminuria" is defined as between about 17 and 250 mg of albumin/g of creatinine for men, and between about 25 and 355 mg/g of creatinine for women. These values are equivalent to: (a) between about 30 and 300 µg/min albumin excretion rate in timed urine collections or (b) between about 40-430 mg of protein excreted in a 24-hour urine collection.

As used herein, "proteinuria" is defined as greater than about 250 mg of albumin/g of creatinine for men, and greater than about 355 mg/g for women. These values are equivalent to: (a) greater than about 300 µg/min albumin excretion rates in timed urine collections, or (b) greater than about 430 mg of protein excreted in a 24-hour urine collection.

As used herein, "normoalbuminuria" is less than 17 mg of albumin/g of creatinine for men, and less than 25 mg/g for women. Equivalent values are less than 30 µg/min albumin excretion rate in timed urine collection or less than 43 mg of protein excreted in a 24 hour period.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, useful methods and materials are described below. The materials, methods, and examples are illustrative only and not intended to be limiting. The details of one or more embodiments of the invention are set forth in the accompanying drawings and the description below. Other features, objects, and advantages of the invention will be apparent from the description and drawings, and from the claims.

DETAILED DESCRIPTION

Figure 1:
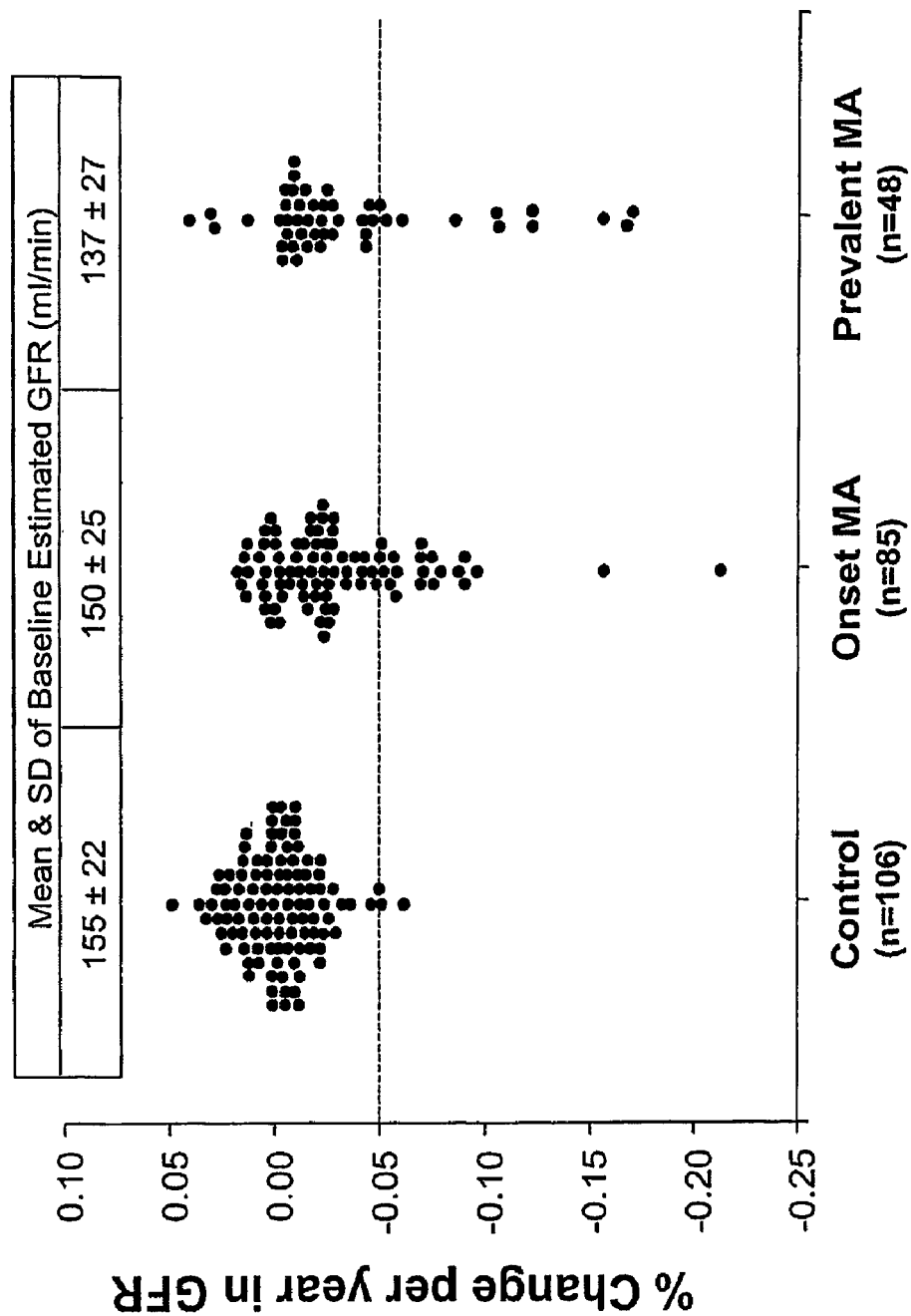
FIG. 1 is a scatter graph comparing the percent change per year of glomerular filtration rate (GFR) (renal function) in individuals in three different study groups: 1) a control group in which individuals did not have MA, 2) a group of individuals who developed MA during the course of the study, and 3) a group of individuals who had MA at the start of the study.

The invention is based, in part on the inventors' discovery that declining renal function occurs in a substantial proportion of patients at risk for renal disease (e.g., diabetic patients) before overt symptoms of renal disease are present, e.g., in patients with normoalbuminuria or microalbuminuria. The inventors have further found that a particular profile of chemokines and/or cytokines or other proteins (e.g., levels of MCP-1, IL-8, IP-10, MIF, FGF-2, PDGF-AA, uPA, uPAR, and/or fibronectin) in the subject (e.g., in the urine of the subject) can predict a decline in renal function in the absence of overt symptoms of renal disease. Thus, evaluation of one or more of: MCP-1, IL-8, IP-10, MIF, FGF-2, PDGF-AA, uPA, uPAR, and fibronectin in the subject allows for evaluation of declining renal function at a much earlier stage in the pathogenesis of renal disease than can be evaluated by direct measures of renal function. Accordingly, the invention features methods of detecting loss of renal function; methods of evaluating the risk, severity or stage of renal disease (e.g., diabetic nephropathy or ESRD); methods of monitoring the effects of treatments for renal disease; and methods of treating renal disease. Also included are reagents and kits useful to perform the methods described herein.

Renal Disease

Over the last two decades, the risk of developing renal failure (end stage renal disease or ESRD) in individuals with diabetes rose steadily despite increasingly widespread use of seemingly effective treatment with antihypertensive drugs, including ACE inhibitors. The increasing risk of ESRD is particularly pronounced in type 2 diabetes but is also seen in type 1 diabetes (T1DM). The causes of this epidemic of ESRD are unknown.

Onset of microalbuminuria (MA) is a very frequent event in patients with T1DM, but half of the patients who develop MA regress to normoalbuminuria within several years (Scott et al. *Diabetes* 2001; 50:2842-49). Less than half of the patients with MA progress to proteinuria (Warram et al. *Diabetes* 2000; 49:94-100).

The inventors have now found that about one quarter of the patients who develop MA begin to lose renal function at a clinically significant rate soon after the onset of MA, and this loss seems to progress unabated over time (see examples herein). Previously, renal function loss was thought to begin at the stage of proteinuria Early renal function loss is associated with elevated urinary levels of certain chemokines (Table 4). This points to the importance of inflammation in renal tubules and interstitium as a mechanism of the early renal function loss.

In a previous study of a cohort of individuals with T1DM diagnosed in 1959 and followed until 1995, ESRD developed in 25% of them, the onsets occurring after 13 to 35 years of diabetes (Krolewski et al. *Kidney Int* 1996; 50:2041-46). A recent analysis of U.S. population data spanning the last 20 years revealed that the risk of ESRD has increased steeply in type 2 diabetes and gradually in T1DM. This epidemic occurred despite increasing prevalence of treatment with antihypertensive drugs as well as ACE inhibitors. The follow-up data, described herein, indicate no association between treatment with ACE inhibitors and renal function loss in patients with T1DM and MA. All these findings indicate that despite the evidence in clinical trials that ACE inhibitors are effective in retarding renal function loss, the risk of developing ESRD has not decreased at the population level.

The methods disclosed herein will allow effective and simple methods to identify and treat individuals at risk of early loss of renal function.

The inventors have found that detection of one or more of the cytokines or chemokines IL-8 (Interleukin 8, also called chemotactic cytokine), IP-10 (Interferon-inducible Protein-10), MCP-1 (Monocyte Chemoattractant Protein 1), MIF (Monocyte Inhibitory Factor), FGF-2 (Fibroblast Growth Factor 2), and PDGF-AA (Platelet-Derived Growth Factor); the protease uPA (urokinase plasminogen activator); uPAR (urokinase-type plasminogen activator receptor); and fibronectin in a biological sample (e.g., a urine sample) of a subject, e.g., a human, can be an indicator for early loss of renal function, e.g., before onset of proteinuria. The methods and compositions of the invention thus provide simple, reliable and reproducible means to evaluate a subject, e.g., a person, for risk, severity or stage of renal disease, e.g., for risk of early loss of renal function or developing ESRD. The methods described herein can be used earlier in the progression of renal disease than methods that provide direct measures of renal function, such as serum creatinine level. Serum creatinine level, the most commonly used surrogate measure of glomerular filtration rate (hereafter referred to as GFR or renal function), does not increase until renal function decreases to less than 50% of its normal value. The methods described herein detect loss of renal function at a much earlier stage.

Diagnostic/Monitoring Assays

The inventors discovered that a significant number of individuals at risk for ESRD, e.g., individuals with T1DM or microalbuminuria, are at risk for early loss of renal function. The diagnostic methods described herein can identify those subjects at risk for early loss of renal function. The diagnostic methods of the invention provide a method of evaluating a subject, such as a human. The method includes evaluating the gene, presence, level, activity or expression of one or more of IL-8, MCP-1, IP-10, MIF, FGF-2, PDGF-AA, uPA, uPAR, and fibronectin, in a biological sample of the subject. The biological sample can be a urine or serum sample, or a blood, tissue, or other such sample. An aberrant gene, presence, level, activity or expression of one or more of these molecules can be correlated with a prognosis, stage or severity of risk for loss of renal function.

The presence, level, or absence of a protein described herein in a biological sample can be evaluated by obtaining a biological sample from a test subject (e.g., a urine sample) and contacting the biological sample with a compound or an agent capable of detecting the protein, or nucleic acid (e.g., mRNA, genomic DNA) that encodes the protein, such that the presence of the protein or nucleic acid is detected in the biological sample. The term "biological sample" includes tissues, cells and biological fluids isolated from a subject, as well as tissues, cells and fluids present within a subject. A preferred biological sample is a urine sample. The level of expression of a protein described herein, e.g., a chemokine or cytokine, can be measured in a number of ways, including, but not limited to: measuring the amount of protein encoded by a gene, e.g., a chemokine or cytokine gene; measuring the mRNA encoded by the gene, e.g., the chemokine or cytokine gene; and/or measuring the activity of the protein encoded by the gene.

A variety of methods can be used to determine the level of a protein described herein encoded by a gene, e.g., a chemokine or cytokine gene. In general, these methods include contacting an agent that selectively binds to the protein, such as an antibody, with a sample to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled," with regard to the probe or antibody, is intended to encompass direct labeling of the probe or antibody by coupling (i.e., physically liking) a detectable substance to the probe or antibody, as well as indirect labeling of the probe or antibody by reactivity with a detectable substance. Examples of detectable substances are provided herein.

The detection methods can be used to detect a protein described herein, e.g., a chemokine or cytokine, such as IL-8, MCP-1, IP-10, MIF, FGF-2, and/or PDGF-AA; uPA; uPAR; and/or fibronectin in a biological sample in vitro as well as in vivo. In vitro techniques for detection of a protein described herein, e.g., a chemokine or cytokine, include enzyme linked immunosorbent assays (ELISAs), immunoprecipitations, immunofluorescence, enzyme immunoassay (EIA), radioimmunoassay (RIA), Western blot analysis, and Luminex™×MAP™ detection assay. In vivo techniques for detection of a protein described herein, e.g., a chemokine or cytokine such as IL-8, MCP-1, IP-10, MIF, FGF-2, or PDGF-AA, include introducing into a subject a labeled antibody that detects the protein, e.g., the chemokine or cytokine. For example, the antibody can be labeled with a radioactive marker whose presence and location in a subject can be detected by standard imaging techniques. In another embodiment, the sample is labeled, e.g., biotinylated and then contacted to the antibody, e.g., an antibody positioned on an antibody array. The sample can be detected, e.g., with avidin coupled to a fluorescent label.

Immunoassays

The presence, level, expression, or activity of a protein described herein, e.g., a chemokine or cytokine such as IL-8, MCP-1, IP-10, MIF, FGF-2, or PDGF-AA; uPA; uPAR; or fibronectin can be evaluated in a variety of ways well known in the art, such as immunoassay, e.g., immunoprecipitation, Western blot analysis (immunoblotting), ELISA, fluorescence-activated cell sorting (FACS), and bead-based detection assays, such as the Luminex™×MAP™ detection technology provided by the MultiAnalyte Profiling Kit (Luminex Corporation, Austin, Tex.). Typically, the level of protein and/or activity, e.g., chemokine or cytokine protein or activity, in a subject sample is compared to the level and/or activity in a control, e.g., the level and/or activity in a tissue from a non-disease subject.

Various types of immunoassays are known in the art. One example of an immunoassay is a "sandwich" type assay, in which a target analyte(s) such as MCP-1, IL-8, IP-10, MIF, FGF-2, PDGF-AA, uPA, uPAR, and/or fibronectin is "sandwiched" between a labeled antibody and an antibody immobilized onto a solid support. The assay is read by observing the presence and amount of antigen-labeled antibody complex bound to the immobilized antibody. Another immunoassay useful in the methods and kits described herein is a "competition" type immunoassay, wherein an antibody bound to a solid surface is contacted with a sample (e.g., a urine sample) containing both an unknown quantity of antigen analyte and with labeled antigen of the same type. The amount of labeled antigen bound on the solid surface is then determined to provide an indirect measure of the amount of antigen analyte in the sample. Such immunoassays are readily performed in a "dipstick" or other test device format (e.g., a flow-through or migratory dipstick or other test device design) for convenient use, e.g., home use or use by a health care provider. For example, numerous types of dipstick immunoassays assays are described in U.S. Pat. No. 5,656,448.

A test device, e.g., a "dipstick", refers to a substrate, preferably a substrate that is insoluble in aqueous solution, e.g., a urine or blood sample, onto which an agent described herein, e.g., an agent that detects a protein described herein, e.g., an antibody described herein, is immobilized. The agent can be applied as a layer on the substrate, or can also penetrate into the substrate. A test device can be a substrate, e.g., a membrane, e.g., a membrane strip, onto which an agent described herein is immobilized. A test device can include a housing for the substrate, e.g., a membrane, e.g., a membrane strip, onto which an agent described herein is immobilized. In one embodiment, the substrate is a substrate other than glass, and is preferably flexible.

In one embodiment, the substrate, e.g., the membrane, e.g., the membrane strip, is, e.g., between about 0.1 and 0.5 inches in width, e.g., between about 0.2 and 0.4, e.g., between about 0.25 and 0.3 inches in width, and is, e.g., between about 1 and 4 inches in length, e.g., between about 2 and 3 inches in length. In one embodiment, an agent described herein, e.g., an antibody described herein, covers an area of the substrate, e.g., the membrane, e.g., the membrane strip, that is greater than about 0.01 cm$^2$, e.g., greater than about 0.1, 0.5, or 1 cm$^2$.

In one embodiment, the test device includes a marker indicating how far to "dip" the substrate into a biological sample, e.g., urine.

In one embodiment, a method described herein employs a dipstick or other test device format to measure the presence, level, expression or activity of a protein described herein, e.g., a chemokine or cytokine described herein (such as IL-8, MCP-1, IP-10, MIF, FGF-2, and/or PDGF-AA), uPA, uPAR, and/or fibronectin. A dipstick or other test device assay can, for example, provide a color indication for an increased risk for accelerated ESRD based upon the levels of a protein described herein, such as IL-8, MCP-1, IP-10, MIF, FGF-2, PDGF-AA, uPA, uPAR, or fibronectin, in a sample, e.g., a urine sample. In one scenario, the dipstick or other test device can react to produce one color if a level of a first protein, e.g., MCP-1, is exceeded, a different color if a level of a second protein, e.g., IL-8, is exceeded, and when both levels are exceeded, the two colors will combine to yield a third color that is easily distinguishable from the others. For example, a dipstick or other test device that turns yellow when a level of MCP-1 is exceeded, and turns blue when a level of IL-8 is exceeded will turn green when both levels are exceeded. A dipstick or other test device-based assay optionally includes an internal negative or positive control.

A dipstick or other test device-based assay could find use in a clinical setting by quickly and reliably indicating a heightened risk for ESRD. This could save valuable time by allowing the physician to initiate treatment sooner, thereby minimizing the harmful effects of the disease.

In another embodiment, the method of the present invention may be utilized in combination with a densitometer or generally a device for measuring light intensity, transmittance, reflection or refraction, or for measuring the wavelength of light as a measure of assay result. Such a device can be used in a setting such as a doctor's office, a clinic or a hospital. The densitometer or other device can provide rapid measurement of the optical density of dipstick or other test device strips that have been contacted with a bodily fluid or tissue.

In a preferred embodiment, a change in color, density, or other parameter can be read by the naked eye.

In a preferred embodiment, the assay can be read without the addition of a reagent not already on the substrate.

Another possible approach to a diagnostic assay includes the use of electrochemical sensor strips, such as those used for home glucose testing, onto which a sample is placed, and which strips include reagents for initiating a reaction when wetted by the sample. The sensor strip is inserted into a meter that measures, e.g., diffusion-limited current of a reaction species indicative of the analyte of interest, such as IL-8, MCP-1, IP-10, MIF, FGF-2, PDGF-AA, uPA, uPAR, or fibronectin. The meter then yields a display indicative of the concentration of analyte in the sample.

Tom et al., U.S. Pat. No. 4,366,241, and Zuk, EP-A 0 143 574 describe migration type assays in which a membrane is impregnated with the reagents needed to perform the assay. An analyte detection zone is provided in which labeled analyte is bound and assay indicia are read.

Bernstein, U.S. Pat. No. 4,770,853, May et al., WO 88/08534, and Ching et al., EP-A 0 299 428 describe migration assay devices that incorporate within them reagents that have been attached to colored direct labels, thereby permitting visible detection of the assay results without addition of further substances.

Valkirs et al., U.S. Pat. No. 4,632,901, disclose a flow-through type immunoassay device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample.

Korom et al., EP-A 0 299 359, discloses a variation in the flow-through device in which the labeled antibody is incorporated into a membrane that acts as a reagent delivery system.

Baxter et al., EP-A 0 125 118, disclose a sandwich type dipstick immunoassay in which immunochemical components such as antibodies are bound to a solid phase. The assay device is "dipped" for incubation into a sample suspected of containing unknown antigen analyte. Enzyme-labeled antibody is then added, either simultaneously or after an incubation period. The device next is washed and then inserted into a second solution containing a substrate for the enzyme. The enzyme-label, if present, interacts with the substrate, causing the formation of colored products that either deposit as a precipitate onto the solid phase or produce a visible color change in the substrate solution.

Kali et al., EP-A 0 282 192, disclose a dipstick device for use in competition type assays.

Rounds in U.S. Pat. No. 4,786,589 describes a dipstick immunoassay device in which the antibodies have been labeled with formazan.

The diagnostic methods can be used in combination with methods of measuring albumin levels in urine, including the methods of radioimmunoassay, immunonephelometry or immunoturbidimetry.

Genotyping and Expression Profiling

Another method of evaluating a protein described herein, e.g., a chemokine or cytokine, e.g., IL-8, MCP-1, IP-10, MIF, FGF-2, or PDGF-AA; uPA; uPAR; or fibronectin protein, in a subject is to determine the presence or absence of a lesion in, or the misexpression of, particularly the overexpression of a gene that encodes the protein. The method includes one or more of the following:

detecting, in a tissue of the subject, the presence or absence of a mutation that affects the expression of a gene encoding a protein described herein, e.g., a chemokine or cytokine, or detecting the presence or absence of a mutation in a region that controls the expression of the gene, e.g., a mutation in the 5' control region;

detecting, in a tissue of the subject, the presence or absence of a mutation that alters the structure of a gene encoding a protein described herein;

detecting, in a tissue of the subject, the misexpression of a gene encoding a protein described herein, at the mRNA level, e.g., detecting a non-wild type level, particularly an increased level, of an mRNA; and detecting, in a tissue of the subject, the misexpression of the gene, at the protein level, e.g., detecting a non-wild type level, particularly an increased level, of a polypeptide.

In preferred embodiments the method includes: ascertaining the existence of at least one of: a deletion of one or more nucleotides from a gene encoding a protein described herein, e.g., a chemokine or cytokine; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence that hybridizes to a sense or antisense sequence from a gene encoding a protein described herein, e.g., a chemokine or cytokine, or naturally occurring mutants thereof or 5' or 3' flanking sequences naturally associated with the gene; (ii) exposing the probe/primer to nucleic acid of a tissue; and detecting, by hybridization, e.g., in situ hybridization, of the probe/primer to the nucleic acid, the presence or absence of the genetic lesion.

Detecting the misexpression, e.g., overexpression, of, e.g., a chemokine or cytokine, includes ascertaining the existence of at least one of: an alteration in the level of a messenger RNA transcript of a gene encoding, e.g., a chemokine or cytokine; the presence of a non-wild type splicing pattern of a messenger RNA transcript of the gene; or a non-wild type level of a gene encoding, e.g., a chemokine or cytokine.

The prognostic assays described herein can be used to determine whether a subject can be administered an agent (e.g., an agent that modulates a protein described herein such as a chemokine or cytokine, e.g., an agent described herein) to prevent or slow the progression to ESRD.

The level of mRNA corresponding to a gene encoding a protein described herein, e.g., a chemokine or a cytokine, in a cell can also be used as a method to monitor for protein expression levels. Levels of mRNA can be determined by in situ and by in vitro formats.

Isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length nucleic acid, or a portion thereof, such as an oligonucleotide of at least 7, 15, 30, 50, 100, 250 or 500 nucleotides in length and sufficient to specifically hybridize under stringent conditions to mRNA or genomic DNA of, e.g., a chemokine or cytokine such as IL-8, MCP-1, IP-10, MIF, FGF-2 or PDGF-AA; uPA; uPAR; or fibronectin. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the gene of a protein described herein, e.g., a chemokine or cytokine described herein, uPA, uPAR, or fibronectin.

The level of mRNA in a sample that is encoded by a gene can be evaluated with nucleic acid amplification, e.g., by RT-PCR (Mullis (1987) U.S. Pat. No. 4,683,202), ligase chain reaction (Barany, *Proc. Natl. Acad. Sci. USA* 88:189-193) (1991), self sustained sequence replication (Guatelli et al., *Proc. Natl. Acad. Sci. USA* 87:1874-1878, 1990), transcriptional amplification system (Kwoh et al., *Proc. Natl. Acad. Sci. USA* 86:1173-1177, 1989), Q-Beta Replicase (Lizardi et al., *BioTechnology* 6:1197, 1988), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the gene being analyzed.

In another embodiment, the methods further include contacting a control sample with a compound or agent capable of detecting mRNA, or genomic DNA, of a protein described herein (such as a chemokine, a cytokine, uPA, uPAR, or fibronectin), and comparing the presence of the mRNA or genomic DNA in the control sample with the presence of mRNA or genomic DNA of a protein described herein in the test sample. In still another embodiment, serial analysis of gene expression, as described in U.S. Pat. No. 5,695,937, is used to detect transcript levels of a protein described herein.

In one embodiment a kit is provided that includes an agent, e.g., a nucleic acid, that detects a gene or RNA of a protein described herein, e.g., a chemokine or cytokine described herein, uPA, uPAR, or fibronectin, and instructions for use in diagnosis or monitoring of stage, severity or risk of renal disease in a subject. The agent, e.g., a nucleic acid probe for a nucleic acid encoding a protein described herein, e.g., a chemokine or a cytokine described herein, uPA, uPAR, or fibronectin can be immobilized on a solid phase, e.g., on a microtiter well, tube, dipstick or other test device, e.g., a polystyrene microtiter well, tube dipstick or other test device. Examples of dipstick or other test device type assays for nucleic acids are described in, e.g., U.S. Pat. No. 5,514,785, U.S. Pat. No. 5,871,906, and U.S. Pat. No. 6,268,128.

The sequence of human IP-10 is known (Luster et al. 1987 *Mol. Cell. Biol.* 7:3723-3731):

(SEQ ID NO:1)
MNQTAILICC LIFLTLSGIQ GVPLSRTVRC TCISISNQPV

NPRSLEKLEI IPASQFCPRV EIIATMKKKG EKRCLNPESK

AIKNLLKAVS KERSKRSP

The sequence of human MCP-1 is known (Yoshimura et al. 1989 *FEBS Lett.* 244:487-93): QPDAINAPVT CCYNFT-NRKI SVQRLASYRR ITSSKCPKEA VIFKTIVAKE ICADPKQKWV QDSMDHLDKQ TQTPKT (SEQ ID NO:2; without signal peptide)

The sequence of human IL-8 is known (Mukaida et al. 1989 *J. Immunol.* 143:1366-71): MTSKLAVALL AAFLISAALC EGAVLPRSAK ELRCQCIKTY SKPFHPKFIK ELRVIES-GPH CANTEIIVKL SDGRELCLDP KENWVQRVVE KFLKRAENS (SEQ ID NO:3)

The sequence of human MIF is known (Weiser et al. 1989 *Proc. Natl. Acad. Sci. U.S.A.* 86:7522-26): MPMFIVNTNV PRASVPDGFL SELTQQLAQA TGKPPQYIAV HVVP-DQLMAF GGSSEPCALC SLHSIGKIGG AQNRSYSKLL CGLLAERLRI SPDRVYINYY DMNAANVGWN NSTFA (SEQ ID NO:4)

Accordingly, antibodies and other agents that detect each of the proteins described herein can be readily made by the skilled artisan.

Treatment Methods

The invention includes a method of treating a subject that includes identifying a normo- or microalbuminuric subject, and modulating the protein level or activity of a protein described herein, e.g., a chemokine or cytokine described herein, e.g., MCP-1, IL-8, IP-10 MIF, FGF-2, and/or PDGF-AA; uPA; uPAR, and/or fibronectin, in the subject. In one aspect, the subject has one or both of diabetes and hypertension. In one aspect modulating MCP-1, IL-8, IP-10, MIF, FGF-2, PDGF-AA, uPA, uPAR, or fibronectin entails administering an antagonist of IL-8, IP-10, MCP-1, MIF, FGF-2, PDGF-AA, uPA, uPAR, or fibronectin activity. The antagonist can be, for example, an antibody, a small molecule inhibitor, or a chemically modified protein, e.g., a chemically modified chemokine, cytokine, uPA, uPAR, or fibronectin.

Antagonists

The overproduction of chemokines in response to renal damage has been implicated in the deterioration of renal function and the progression to ESRD (rev. in Anders et al, *Kidney Intl.* 63:401-415, 2002). Thus treatment of a subject with normal- or microalbuminuria with a protein described herein, e.g., a chemokine or cytokine antagonist, such as an IP-10, IL-8, MCP-1, MIF, FGF-2, or PDGF-AA antagonist; a uPA antagonist; a uPAR antagonist; or a fibronectin antagonist, can prevent the accelerated loss of renal function in MA patients. Numerous IP-10, IL-8, MCP-1, MIF, FGF-2, PDGF-AA, uPA, uPAR, and fibronectin antagonists are known in the art. Others can be identified by art-recognized techniques, e.g., the techniques that follow.

Primary High-Through-Put Methods for Screening Libraries of Peptide Fragments or Homologs Various techniques are known in the art for screening peptides, e.g., synthetic peptides, antibodies or antigen binding fragments thereof, small molecular weight peptides (e.g., linear or cyclic peptides) or generated mutant gene products. Techniques for screening large gene libraries often include cloning the gene library into replicable expression vectors, transforming appropriate cells with the resulting library of vectors, and expressing the genes under conditions in which detection of a desired activity, e.g., binding to a natural ligand, e.g., a receptor or substrate, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays can be used to identify a protein that interacts with a protein described herein, e.g., a chemokine or cytokine described herein (e.g., IL-8, MCP-1, IP-10, MIF, FGF-2, or PDGF-AA), uPA, uPAR, or fibronectin, or active fragments thereof. These may include, e.g., agonists, superagonists, and antagonists of protein activity, e.g., chemokine or cytokine activity, protease activity, or substrate binding activity. These assays rely on detecting the reconstitution of a functional transcriptional activator mediated by protein-protein interactions with a bait protein. In particular, these assays make use of chimeric genes that express hybrid proteins. The first hybrid comprises a DNA-binding domain fused to the bait protein, e.g., a protein described herein, e.g., a chemokine or cytokine (e.g., IL-8, MCP-1, IP-10, MIF, FGF-2, or PDGF-AA), uPA, uPAR, or fibronectin, or active fragments thereof. The second hybrid protein contains a transcriptional activation domain fused to a "prey" protein, e.g., an expression library. If the prey and bait proteins are able to interact, they bring into close proximity the DNA-binding and transcriptional activator domains. This proximity is sufficient to cause transcription of a reporter gene that is operably linked to a transcriptional regulatory site that is recognized by the DNA binding domain, and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. *Bio/Technology* 9:1370-1371, 1991; and Goward et al., *TIBS* 18:136-140, 1992). This technique was used in Sahu et al. (*J. Immunology* 157:884-891, 1996) to isolate an inhibitor of a target protein. In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and fl are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al, *J. Biol. Chem.* 267:16007-16010, 1992; Griffiths et al., *EMBO J* 12:725-734, 1993; Clackson et al., *Nature* 352:624-628, 1991; and Barbas et al., *PNAS* 89:4457-4461, 1992).

A common approach uses the maltose receptor of *E. coli* (the outer membrane protein, LamB) as a peptide fusion partner (Charbit et al., *EMBO* 5:3029-3037, 1986). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al., *Vaccines* 91:387-392, 1991), PhoE (Agterberg, et al., *Gene* 88:37-45, 1990), and PAL (Fuchs et al., *Bio/Tech* 9:369-1372, 1991), as well as large bacterial surface structures have served as vehicles for peptide display. Peptides can be fused to pilin, a protein which polymerizes to form the pilus-a conduit for interbacterial exchange of genetic information (Thiry et al., *Appl. Environ. Microbiol.* 55:984-993, 1989). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al., *Bio/Tech.* 6:1080-1083, 1988). Surface proteins of other bacterial species have also served as peptide fusion partners. Examples include the *Staphylococcus* protein A and the outer membrane protease IgA of *Neisseria* (Hansson et al., *J. Bacteriol.* 174:4239-4245, 1992, and Klauser et al., *EMBO J.* 9:1991-1999, 1990).

In the filamentous phage systems and the LamB system described above, the physical link between the peptide and its encoding DNA occurs by the containment of the DNA within a particle (cell or phage) that carries the peptide on its surface.

Capturing the peptide captures the particle and the DNA within. An alternative scheme uses the DNA-binding protein LacI to form a link between peptide and DNA (Cull et al., *PNAS USA* 89:1865-1869, 1992). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al., *Proc. Natl. Acad. Sci. U.S.A.* 89-1869, 1992).

This scheme, sometimes referred to as peptides-on-plasmids, differs in two important ways from the phage display methods. First, the peptides are attached to the C-terminus of the fusion protein, resulting in the display of the library members as peptides having free carboxyl termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla et al., *Proc. Natl. Acad. Sci. U.S.A.* 87:6378-6382, 1990). A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al., *J. Med. Chem.* 37:1233-1251, 1994). These particular biases are not a factor in the LacI display system.

The number of small peptides available in recombinant random libraries is enormous. Libraries of $10^7$-$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3-6 orders of magnitude/larger than the currently available phage/phagemid or plasmid libraries. Furthermore, the construction of the libraries, expression of the peptides, and screening, is done in an entirely cell-free format.

In one application of this method (Gallop et al., *J. Med. Chem.* 37:1233-1251, 1994), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret et al., *Anal. Biochem* 204: 357-364, 1992). To identify the sequences of the active peptides one sequences the DNA produced by the phagemid host.

Secondary Screens for Protein Modulators

The high through-put assays described above can be followed (or substituted) by secondary screens in order to identify biological activities that will, e.g., allow one skilled in the art to differentiate agonists from antagonists. The type of a screen used will depend on the desired activity that needs to be tested. For example, an assay can be developed in which the ability of a candidate agent to modulate tyrosine phosphatase activity can be used to identify antagonists or agonists from a group of peptide fragments isolated though one of the primary screens described above.

In one example, the ability of a test agent to modulate a protein described herein, e.g., a chemokine or cytokine described herein, uPA, uPAR, or fibronectin, can be evaluated by evaluating the ability of the test agent to disrupt the ability of a chosen protein, e.g., IL-8, MCP-1, IP-10, MIF, FGF-2, PDGF-AA, uPA and fibronectin, to bind its receptor. The test agent is contacted with a reaction mixture or cell containing the chosen protein, or a DNA expressing the protein; the corresponding receptor or a cell expression the receptor is contacted with the reaction mixture or cell; the reaction mixture or cell is allowed to incubate for a time and under conditions sufficient for a protein described herein to bind its receptor; and a determination is made of whether the protein bound to its receptor. The result can be compared to a reference, e.g., a control reaction mixture or cell not contacted with the test agent. For example, IP-10 can bind the receptor CXCR3; IL-8 can bind IL-8 receptor A (IL-8 RA) and IL-8 receptor B (IL-8 RB); MCP-1 can bind the receptor CCR2 (e.g., CCR2B); FGF-2 can bind an FGFR (e.g., FGFR1, FGFR2, or FGFR3); PDGF-AA can bind PDGFRα; and uPA can bind uPAR.

Peptide Mimetics

The invention also provides for production of the receptor binding domains of a protein described herein, e.g., a chemokine or cytokine described herein (such as IL-8, MCP- 1, IP-10, MIF, FGF-2, or PDGF-AA), uPA, or fibronectin, to generate mimetics, e.g. peptide or non-peptide agents, e.g., inhibitory agents. See, for example, "Peptide inhibitors of human papillomavirus protein binding to retinoblastoma gene protein" European patent applications EP 0 412 762 and EP 0 031 080.

Non-hydrolyzable peptide analogs of critical residues can be generated using benzodiazepine (e.g., see Freidinger et al. in *Peptides: Chemistry and Biology*, ed. by G. R. Marshall, ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al., *J Med Chem* 29:295, 1986, and Ewenson et al. in *Peptides: Structure and Function* (Proceedings of the 9th American Peptide Symposium) Pierce Chemical Co. Rockland, Ill., 1985), β-turn dipeptide cores (Nagai et al., *Tetrahedron Lett* 26:647, 1985, and Sato et al., *J Chem Soc Perkin Trans* 1:1231, 1986), and β-aminoalcohols (Gordon et al., *Biochem Biophys Res Commun* 126:419, 1985; and Dann et al., *Biochem Biophys Res Commun* 134:71, 1986).

Antibodies

An agent described herein, e.g., a modulator of a protein described herein, e.g., a chemokine or cytokine described herein (such as IL-8, MCP-1, IP-10, MIF, FGF-2, or PDGF-AA), uPA, uPAR, or fibronectin, can also be an antibody specifically reactive with a protein described herein. An antibody can be an antibody or a fragment thereof, e.g., an antigen binding portion thereof. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat et al., *Sequences of Proteins of Immunological Interest*, Fifth Edition, U.S. Department of Health and Human Services, NIH Publication No. 91-3242, 1991, and Chothia et al., *J. Mol. Biol.* 196:901-917, 1987, which are incorporated herein by reference). Each VH and VL is composed of three CDR's and four FRs, arranged from amino-terminus to carboxyl-terminus in the following order: FR1, CDR1, FR2, CDR2, FR3, CDR3, FR4.

The antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

The term "antigen-binding fragment" of an antibody (or simply "antibody portion," or "fragment"), as used herein, refers to one or more fragments of a full-length antibody that retain the ability to specifically bind to an antigen (e.g., a polypeptide encoded by a nucleic acid of Group I or II). Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., *Nature* 341:544-546, 1989), which consists of a VH domain; and (vi) an isolated complementarity determining region (CDR). Furthermore, although the two domains of the Fv fragment, VL and VH, are coded for by separate nucleic acids, they can be joined, using recombinant methods, by a synthetic linker that enables them to be made as a single protein chain in which the VL and VH regions pair to form monovalent molecules (known as single chain Fv (scFv); see e.g., Bird et al., *Science* 242:423-426, 1988, and Huston et al., *Proc. Natl. Acad. Sci. USA* 85:5879-5883, 1988). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. The term "monoclonal antibody" or "monoclonal antibody composition", as used herein, refers to a population of antibody molecules that contain only one species of an antigen binding site capable of immunoreacting with a particular epitope. A monoclonal antibody composition thus typically displays a single binding affinity for a particular protein with which it immunoreacts.

Anti-protein/anti-peptide antisera or monoclonal antibodies can be made as described herein by using standard protocols (See, for example, *Antibodies: A Laboratory Manual* ed. by Harlow and Lane, Cold Spring Harbor Press, 1988).

A protein described herein, e.g., a chemokine or cytokine described herein (such as IL-8, MCP-1, IP-10, MIF, FGF-2, or PDGF-AA), uPA, uPAR, or fibronectin, can be used as an immunogen to generate antibodies that bind the component using standard techniques for polyclonal and monoclonal antibody preparation. The full-length component protein can be used or, alternatively, antigenic peptide fragments of the component can be used as immunogens.

Typically, a peptide is used to prepare antibodies by immunizing a suitable subject, (e.g., rabbit, goat, mouse or other mammal) with the immunogen. An appropriate immunogenic preparation can contain, for example, a recombinant form of a protein described herein, e.g., a chemokine or cytokine described herein(e.g., IL-8, MCP-1, IP-10, MIF, FGF-2, or PDGF-AA), uPA, uPAR, or fibronectin; recombinant peptide; or a chemically synthesized protein described herein, e.g., a chemokine or cytokine described herein (e.g., IL-8, MCP-1, IP-10, MIF, FGF-2, or PDGF-AA), uPA, uPAR, or fibronectin; chemically synthesized peptide or antagonist. See, e.g., U.S. Pat. No. 5,460,959; and co-pending U.S. applications U.S. Ser. No. 08/334,797; U.S. Ser. No. 08/231,439; U.S. Ser. No. 08/334,455; and U.S. Ser. No. 08/928,881, which are hereby expressly incorporated by reference in their entirety. The nucleotide and amino acid sequences of IL-8, MCP-1, IP-10, MIF, FGF-2, PDGF-AA, uPA, uPAR, and fibronectin described herein are known. The preparation can further include an adjuvant, such as Freund's complete or incomplete adjuvant, or similar immunostimulatory agent. Immunization of a suitable subject with an immunogenic protein described herein, e.g., IL-8, MCP-1, IP-10, MIF, FGF-2, PDGF-AA, uPA, uPAR, or fibronectin, or fragment preparation induces a polyclonal antibody response.

Additionally, antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al., *Science* 240:1041-1043, 1988; Liu et al., *PNAS* 84:3439-3443, 1987; Liu et al., *J. Immunol.* 139:3521-3526, 1987; Sun et al., *PNAS* 84:214-218, 1987; Nishimura et al., *Canc. Res.* 47:999-1005, 1987; Wood et al., *Nature* 314:446-449, 1985; and Shaw et al., *J. Natl. Cancer Inst.* 80:1553-1559, 1988); Morrison, S. L., *Science* 229:1202-1207, 1985; Oi et al., *BioTechniques* 4:214, 1986; Winter U.S. Pat. No. 5,225,539; Jones et al., *Nature* 321:552-525, 1986; Verhoeyan et al., *Science* 239:1534, 1988; and Beidler et al., *J. Immunol.* 141: 4053-4060, 1988.

In addition, a human monoclonal antibody directed against a protein described herein, e.g., a chemokine or cytokine (such as IL-8, MCP-1, IP-10, MIF, FGF-2, or PDGF-AA), uPA, uPAR, or fibronectin, can be made using standard techniques. For example, human monoclonal antibodies can be generated in transgenic mice or in immune deficient mice engrafted with antibody-producing human cells. Methods of generating such mice are describe, for example, in Wood et al. PCT publication WO 91/00906; Kucherlapati et al. PCT publication WO 91/10741; Lonberg et al. PCT publication WO 92/03918; Kay et al. PCT publication WO 92/03917; Kay et al. PCT publication WO 93/12227; Kay et al. PCT publication WO 94/25585; Rajewsky et al. PCT publication WO 94/04667; Ditullio et al. PCT publication WO 95/17085; Lonberg et al., *Nature* 368:856-859, 1994; Green et al., *Nature Genet.* 7:13-21, 1994; Morrison et al., *Proc. Natl. Acad. Sci. USA* 81:6851-6855, 1994; Bruggeman et al., *Year Immunol* 7:33-40, 1993; Choi et al., *Nature Genet.* 4:117-123, 1993; Tuaillon et al., *PNAS* 90:3720-3724, 1993; Bruggeman et al., *Eur J Immunol* 21:1323-1326, 1991; Duchosal et al. PCT publication WO 93/05796; U.S. Pat. No. 5,411,749; McCune et al., *Science* 241:1632-1639, 1988; Kamel-Reid et al., *Science* 242:1706, 1988; Spanopoulou, *Genes & Development* 8:1030-1042, 1994; and Shinkai et al., *Cell* 68:855-868, 1992. A human antibody-transgenic mouse or an immune deficient mouse engrafted with human antibody-producing cells or tissue can be immunized with a protein described herein, e.g., a chemokine or cytokine described herein (e.g., IL-8, MCP-1, IP-10, MIF, FGF-2, PDGF-AA), uPA, uPAR, or fibronectin, or an antigenic peptide thereof, and splenocytes from these immunized mice can then be used to create hybridomas. Methods of hybridoma production are well known.

Human monoclonal antibodies against a protein described herein, e.g., a chemokine or cytokine described herein (e.g., IL-8, MCP-1, IP-10, MIF, FGF-2, or PDGF-AA), uPA, uPAR, or fibronectin, can also be prepared by constructing a combinatorial immunoglobulin library, such as a Fab phage display library or a scFv phage display library, using immunoglobulin light chain and heavy chain cDNAs prepared from mRNA derived from lymphocytes of a subject. See, e.g., McCafferty et al. PCT publication WO 92/01047; Marks et al., *J. Mol. Biol.* 222:581-597, 1991; and Griffiths et al., *EMBO J* 12:725-734, 1993. In addition, a combinatorial library of antibody variable regions can be generated by mutating a known human antibody. For example, a variable region of a human antibody known to bind a protein described herein can be mutated by, for example, using randomly altered mutagenized oligonucleotides, to generate a library of mutated variable regions which can then be screened to bind to a protein described herein, e.g., a chemokine or cytokine described herein (e.g., IL-8, MCP-1, IP-10, MIF, FGF-2, or PDGF-AA), uPA, uPAR, or fibronectin. Methods of inducing random mutagenesis within the CDR regions of immunoglobin heavy and/or light chains, methods of crossing randomized heavy and light chains to form pairings and screening methods can be found in, for example, Barbas et al. PCT publication WO 96/07754; and Barbas et al., *Proc. Nat'l Acad. Sci. USA* 89:4457-4461, 1992.

The immunoglobulin library can be expressed by a population of display packages, preferably derived from filamentous phage, to form an antibody display library. Examples of methods and reagents particularly amenable for use in generating antibody display library can be found in, for example, Ladner et al. U.S. Pat. No. 5,223,409; Kang et al. PCT publication WO 92/18619; Dower et al. PCT publication WO 91/17271; Winter et al. PCT publication WO 92/20791; Markland et al. PCT publication WO 92/15679; Breitling et al. PCT publication WO 93/01288; McCafferty et al. PCT publication WO 92/01047; Garrard et al. PCT publication WO 92/09690; Ladner et al. PCT publication WO 90/02809; Fuchs et al., *Bio/Technology* 9:1370-1372; 1991; Hay et al., *Hum Antibod Hybridomas* 3:81-85, 1992; Huse et al., *Science* 246:1275-1281, 1989; Griffiths et al., 1993, supra; Hawkins et al., *J Mol Biol* 226:889-896, 1992; Clackson et al., *Nature* 352:624-628, 1991; Gram et al., *PNAS* 89:3576-3580, 1992; Garrad et al., *Bio/Technology* 9:1373-1377, 1991; Hoogenboom et al., *Nuc Acid Res* 19:4133-4137, 1991; and Barbas et al., *PNAS* 88:7978-7982, 1991. Once displayed on the surface of a display package (e.g., filamentous phage), the antibody library is screened to identify and isolate packages that express an antibody that binds a protein described herein, e.g., a chemokine or cytokine described herein (e.g., IL-8, MCP-1, IP-10, MIF, FGF-2, or PDGF-AA), uPA, uPAR, or fibronectin. In a preferred embodiment, the primary screening of the library involves panning with an immobilized protein described herein, and display packages expressing antibodies that bind immobilized proteins described herein are selected.

Antisense Nucleic Acid Sequences

Nucleic acid molecules that are antisense to a nucleotide encoding a protein described herein, e.g., a chemokine or cytokine described herein (e.g., IL-8, MCP-1, IP-10, MIF, FGF-2, or PDGF-AA), uPA, uPAR, or fibronectin, can also be used as an agent that inhibits expression of a chosen protein. An "antisense" nucleic acid includes a nucleotide sequence that is complementary to a "sense" nucleic acid encoding the component, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to an entire coding strand, or to only a portion thereof. For example, an antisense nucleic acid molecule that is antisense to the "coding region" of the coding strand of a nucleotide sequence encoding the component can be used.

The coding strand sequences encoding proteins described herein are known. Given the coding strand sequences encoding these proteins, antisense nucleic acids can be designed according to the rules of Watson and Crick base pairing. The antisense nucleic acid molecule can be complementary to the entire coding region of mRNA, but more preferably is an oligonucleotide that is antisense to only a portion of the coding or noncoding region of mRNA. For example, the antisense oligonucleotide can be complementary to the region surrounding the translation start site of the mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides that can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

RNAi

Double stranded nucleic acid molecules that can silence protein activity, e.g., silence a protein described herein or its receptor, e.g., silence an IL-8, MCP-1, IP-10, MIF, FGF-2, PDGF-AA, uPA, uPAR, or fibronectin gene, can also be used as agents that inhibit expression of IL-8, MCP-1, IP-10, MIF, FGF-2, PDGF-AA, uPA, uPAR, or fibronectin. RNA interference (RNAi) is a mechanism of post-transcriptional gene silencing in which double-stranded RNA (dsRNA) corresponding to a gene (or coding region) of interest is introduced into a cell or an organism, resulting in degradation of the corresponding mRNA. The RNAi effect persists for multiple cell divisions before gene expression is regained. RNAi is therefore an extremely powerful method for making targeted knockouts or "knockdowns" at the RNA level. RNAi has proven successful in human cells, including human embryonic kidney and HeLa cells (see, e.g., Elbashir et al. Nature 2001 May 24;411(6836):494-8). In one embodiment, gene silencing can be induced in mammalian cells by enforcing endogenous expression of RNA hairpins (see Paddison et al., 2002, PNAS USA 99:1443-1448). In another embodiment, transfection of small (21-23 nt) dsRNA specifically inhibits gene expression (reviewed in Caplen (2002) Trends in Biotechnology 20:49-51).

Briefly, RNAi is thought to work as follows. dsRNA corresponding to a portion of a gene to be silenced is introduced into a cell. The dsRNA is digested into 21-23 nucleotide siRNAs, or short interfering RNAs. The siRNA duplexes bind to a nuclease complex to form what is known as the RNA-induced silencing complex, or RISC. The RISC targets the homologous transcript by base pairing interactions between one of the siRNA strands and the endogenous mRNA. It then cleaves the mRNA~12 nucleotides from the 3' terminus of the siRNA (reviewed in Sharp et al (2001) Genes Dev 15: 485-490; and Hammond et al. (2001) Nature Rev Gen 2: 110-119).

RNAi technology in gene silencing utilizes standard molecular biology methods. dsRNA corresponding to the sequence from a target gene to be inactivated can be produced by standard methods, e.g., by simultaneous transcription of both strands of a template DNA (corresponding to the target sequence) with T7 RNA polymerase. Kits for production of dsRNA for use in RNAi are available commercially, e.g., from New England Biolabs, Inc. Methods of transfection of dsRNA or plasmids engineered to make dsRNA are routine in the art.

Gene silencing effects similar to those of RNAi have been reported in mammalian cells with transfection of a mRNA-cDNA hybrid construct (Lin et al., Biochem Biophys Res Commun 2001 Mar. 2;281(3):639-44), providing yet another strategy for gene silencing.

Administration

An agent that modulates a protein described herein, e.g., a chemokine or cytokine described herein (e.g., IL-8, MCP-1, IP-10, MIF, FGF-2, or PDGF-AA), uPA, uPAR, or fibronectin, e.g., an agent described herein, can be administered to a subject by standard methods. For example, the agent can be administered by any of a number of different routes including intravenous, intradermal, subcutaneous, oral (e.g., inhalation), transdermal (topical), and transmucosal, or direct administration, e.g., onto the surface of the eye. In one embodiment, the modulating agent can be administered orally. In another embodiment, the agent is administered by injection, e.g., intramuscularly, or intravenously.

The agent that modulates a protein described herein, e.g., a chemokine or cytokine described herein (e.g., IL-8, MCP-1, IP-10, MIF, FGF-2, or PDGF-AA), uPA, uPAR, or fibronectin, e.g., an agent described herein, e.g., nucleic acid molecules, polypeptides, fragments or analogs, modulators, organic compounds and antibodies (also referred to herein as "active compounds") can be incorporated into pharmaceutical compositions suitable for administration to a subject, e.g., a human. Such compositions typically include the nucleic acid molecule, polypeptide, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an agent described herein) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The nucleic acid molecules described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., *PNAS* 91:3054-3057, 1994). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

Gene Therapy

The nucleic acids described herein, e.g., an antisense nucleic acid described herein, can be incorporated into gene constructs to be used as a part of a gene therapy protocol to deliver nucleic acids encoding either an agonistic or antagonistic form of a protein described herein. The invention features expression vectors for in vivo transfection and expression of a protein described herein in particular cell types so as to reconstitute the function of, or alternatively, antagonize the function of the component in a cell in which that polypeptide is misexpressed. Expression constructs of such components may be administered in any biologically effective carrier, e.g. any formulation or composition capable of effectively delivering the component gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA, encoding a protein described herein, e.g., a chemokine or cytokine described herein (e.g., IL-8, MCP-1, IP-10, MIF, FGF-2, or PDGF-AA), uPA, uPAR, or fibronectin. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") that produce only replication-defective retroviruses has increased the utility of retroviruses for gene therapy, and defective retroviruses are characterized for use in gene transfer for gene therapy purposes (for a review see Miller, A. D., *Blood* 76:271) (1990). A replication defective retrovirus can be packaged into virions that can be used to infect a target cell through the use of a helper virus by standard techniques. Protocols for producing recombinant retroviruses and for infecting cells in vitro or in vivo with such viruses can be found in *Current Protocols in Molecular Biology*, ed. by Ausubel et al., Greene Publishing Associates, (1989), Sections 9.10-9.14 and other standard laboratory manuals. Examples of suitable retroviruses include pLJ, pZIP, pWE and pEM that are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see, for example, Eglitis et al., *Science* 230:1395-1398, 1985; Danos et al., *Proc. Natl. Acad. Sci. USA* 85:6460-6464, 1988; Wilson et al., *Proc. Natl. Acad. Sci. USA* 85:3014-3018, 1988; Armentano et al., *Proc. Natl. Acad. Sci. USA* 87:6141-6145, 1990; Huber et al., *Proc. Natl. Acad. Sci. USA* 88:8039-8043, 1991; Ferry et al., *Proc. Natl. Acad. Sci. USA* 88:8377-8381, 1991; Chowdhury et al., *Science* 254:1802-1805, 1991; van Beusechem et al., *Proc. Natl. Acad. Sci. USA* 89:7640-7644, 1992; Kay et al., *Human Gene Therapy* 3:641-647, 1992; Dai et al., *Proc. Natl. Acad. Sci. USA* 89:10892-10895, 1992; Hwu et al., *J. Immunol.* 150:4104-4115, 1993; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al., *BioTechniques* 6:616, 1988; Rosenfeld et al., *Science* 252:431-434, 1991; and Rosenfeld et al., *Cell* 68:143-155, 1992. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al., 1992, cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand et al., *J. Virol.* 57:267, 1986).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (See, e.g., Muzyczka et al., *Curr. Topics in Micro. and Immunol.* 158:97-129, 1992.) It is also one of the few viruses that may integrate its DNA into non-dividing cells, and exhibits a high frequency of stable integration (see, for example, Flotte et al., *Am. J. Respir. Cell. Mol. Biol.* 7:349-356, 1992; Samulski et al., *J. Virol.* 63:3822-3828, 1989; and McLaughlin et al., *J. Virol.* 62:1963-1973, 1989). Vectors containing as little as 300 base pairs of AAV can be packaged and can integrate. Space for exogenous DNA is limited to about 4.5 kb. An AAV vector such as that described in Tratschin et al. (*Mol. Cell. Biol.* 5:3251-3260, 1985) can be used to introduce DNA into cells. A variety of nucleic acids have been introduced into different cell types using AAV vectors (see, for example, Hermonat et al., *Proc. Natl. Acad. Sci. USA* 81:6466-6470, 1984; Tratschin et al., *Mol. Cell. Biol.* 4:2072-2081, 1985; Wondisford et al., *Mol. Endocrinol.* 2:32-39, 1988; Tratschin et al., *J. Virol.* 51:611-619, 1984; and Flotte et al., *J. Biol. Chem.* 268:3781-3790, 1993).

In addition to viral transfer methods, such as those illustrated above, non-viral methods can also be employed to cause expression of a protein described herein, e.g., a chemokine or cytokine described herein (e.g., IL-8, MCP-1, IP-10, MIF, FGF-2, or PDGF-AA), uPA, uPAR, or fibronectin, in the tissue of a subject. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., *J Invest Dermatol.* 116:131-135, 2001; Cohen et al., *Gene Ther* 7:1896-905, 2000; or Tam et al., *Gene Ther* 7:1867-74, 2000.

In a representative embodiment, a gene encoding a protein described herein, e.g., a chemokine or cytokine described herein (e.g., IL-8, MCP-1, IP-10, MIF, FGF-2, or PDGF-AA), uPA, uPAR, or fibronectin, can be entrapped in liposomes bearing positive charges on their surface (e.g., lipofectins) and (optionally) which are tagged with antibodies against cell surface antigens of the target tissue (Mizuno et al., *No Shinkei Geka* 20:547-551, 1992; PCT publication WO91/06309; Japanese patent application 1047381; and European patent publication EP-A-43075).

In clinical settings, the gene delivery systems for the therapeutic gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (see, e.g., Chen et al., *PNAS* 91: 3054-3057, 1994).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells that produce the gene delivery system.

Cell Therapy

A protein described herein, e.g., a chemokine or cytokine described herein (e.g., IL-8, MCP-1, IP-10, MIF, FGF-2, or PDGF-AA), uPA, uPAR, or fibronectin, can be modulated in a subject by introducing into a cell, e.g., an endothelial cell, a nucleotide sequence that modulates the production of a protein or agent described herein, e.g., a nucleotide sequence encoding a protein or agent described herein, a polypeptide or functional fragment or analog thereof, a promoter sequence (e.g., a promoter sequence from a gene encoding a protein or agent described herein or from another gene), an enhancer sequence(e.g., 5' untranslated region (UTR), e.g., a 5' UTR from a gene encoding a protein or agent described herein, or from another gene; or a 3' UTR, e.g., a 3' UTR from gene encoding a protein or agent described herein, or from another gene), a polyadenylation site, an insulator sequence, or another sequence that modulates the expression of a protein or agent described herein. The cell can then be introduced into the subject.

Primary and secondary cells to be genetically engineered can be obtained form a variety of tissues and include cell types which can be maintained propagated in culture. For example, primary and secondary cells include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells (myoblasts) and precursors of these somatic cell types. Primary cells are preferably obtained from the individual to whom the genetically engineered primary or secondary cells are administered. However, primary cells may be obtained for a donor (other than the recipient).

The term "primary cell" includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. Secondary cells are cell strains which consist of secondary cells which have been passaged one or more times.

Primary or secondary cells of vertebrate, particularly mammalian, origin can be transfected with an exogenous nucleic acid sequence which includes a nucleic acid sequence encoding a signal peptide, and/or a heterologous nucleic acid sequence, e.g., encoding a protein described herein, or an agonist or antagonist thereof, and produce the encoded product stably and reproducibly in vitro and in vivo, over extended periods of time. A heterologous amino acid can also be a regulatory sequence, e.g., a promoter that causes expression, e.g., inducible expression or upregulation, of an endogenous sequence. An exogenous nucleic acid sequence can be introduced into a primary or secondary cell by homologous recombination as described, for example, in U.S. Pat. No. 5,641,670, the contents of which are incorporated herein by reference. The transfected primary or secondary cells may also include DNA encoding a selectable marker that confers a selectable phenotype upon them, facilitating their identification and isolation.

Vertebrate tissue can be obtained by standard methods such a punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly or it can be cultured first, removed from the culture plate and resuspended before transfection is carried out. Primary cells or secondary cells are combined with exogenous nucleic acid sequence to, e.g., stably integrate into their genomes, and treated in order to accomplish transfection. As used herein, the term "transfection" includes a variety of techniques for introducing an exogenous nucleic acid into a cell including calcium phosphate or calcium chloride precipitation, microinjection, DEAE-dextrin-mediated transfection, lipofection or electroporation, all of which are routine in the art.

Transfected primary or secondary cells undergo sufficient number doubling to produce either a clonal cell strain or a heterogeneous cell strain of sufficient size to provide the therapeutic protein to an individual in effective amounts. The number of required cells in a transfected clonal heterogeneous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient.

The transfected cells, e.g., cells produced as described herein, can be introduced into an individual to whom the product is to be delivered. Various routes of administration and various sites (e.g., renal sub capsular, subcutaneous, central nervous system (including intrathecal), intravascular, intrahepatic, intraplanchnic, intraperitoneal (including intraomental), and intramuscular implantation) can be used. Once implanted in the individual, the transfected cells produce the product encoded by the heterologous DNA or are affected by the heterologous DNA itself. For example, an individual who suffers from microalbuminuria, or a kidney disorder, is a candidate for implantation of cells producing an antagonist of a protein described herein, e.g., a chemokine or cytokine described herein (e.g., IL-8, MCP-1, IP-10, MIF, FGF-2, or PDGF-AA), uPA, uPAR, or fibronectin.

An immunosuppressive agent e.g., drug, or antibody, can be administered to a subject at a dosage sufficient to achieve the desired therapeutic effect (e.g., inhibition of rejection of the cells). Dosage ranges for immunosuppressive drugs are known in the art. See, e.g., Freed et al., *N. Engl. J. Med.* 327:1549, 1992; Spencer et al., *N. Engl. J. Med.* 327:1541, 1992; and Widner et al., *N. Engl. J. Med.* 327:1556, 1992. Dosage values may vary according to factors such as the disease state, age, sex, and weight of the individual.

Kits

The invention also includes kits for detecting the presence of a protein described herein, e.g., a chemokine or cytokine described herein (e.g., IL-8, MCP-1, IP-10, MIF, FGF-2, or PDGF-AA), uPA, uPAR, or fibronectin, in a biological sample. For example, the kit can include a compound or agent capable of detecting protein (e.g., an antibody) or mRNA (e.g., a nucleic acid probe) of a protein described herein in a biological sample; and a standard. The agent can be coupled to a detectable label, such as a colored, absorbent or fluorescent label. The kit can also include a positive and a negative control, e.g., a reagent that contains a protein described herein, e.g., one or more of IL-8, MCP-1, IP-10, MIF, FGF-2, PDGF-AA, uPA, uPAR, and fibronectin. The instructions can include specific directions for use with a biological sample of a subject that has normoalbuminuria. In some embodiment, the instructions include specific instructions for use with a biological sample of a subject that has, or is at risk for, one or more of: microalbuminuria, diabetes, e.g., T1DM, type 2 diabetes, hypertension, glomerulonephritis, polycystic kidneys, interstitial disease, obstructive uropathy, systemic lupus erythematosus, and multiple myeloma.

The compound or agent can be packaged in a suitable container. The kit can further comprise instructions for using the kit to evaluate a subject, e.g., for risk, staging, or predisposition to a kidney disease, such as diabetic nephropathy or ESRD.

Another embodiment of the present invention is a dipstick or other test device-based kit, suitable for home testing. Such a screening test would provide convenience, privacy and eliminate the necessity and cost of visiting a physician for a screening test, although the dipstick or other test device kit could also be used in a clinical setting. The dipstick or other test device kit could be similar to a home pregnancy kit, known to those of skill in the art, and could provide a color indication for an increased risk for accelerated ESRD based upon the levels of a protein described herein, e.g., a chemokine or cytokine described herein (e.g., IL-8, MCP-1, IP-10, MIF, FGF-2, or PDGF-AA), uPA, uPAR, or fibronectin, in the sample. Such a dipstick or other test device-based kit could be provided with a small plastic cup for collecting and retaining the sample and for conducting the test. In one scenario, the dipstick or other test device can react to produce one color if a level of a first protein, e.g., MCP-1, is exceeded, a different color if a level of a second protein, e.g., IL-8, is exceeded, and when both levels are exceeded, the two colors will combine to yield a third color that is easily distinguishable from the others. For example, a dipstick or other test device that turns yellow when a level of MCP-1 is exceeded, and turns blue when a level of IL-8 is exceeded will turn green when both levels are exceeded. Because a dipstick or other test device-based assay kit would be relatively resistant to temperature and humidity variations, it could easily be transported, stored and used virtually anywhere in the world.

In one embodiment, the kit includes at least 1, e.g., at least 2, 5, 10, 20, 30, or 50, test devices, e.g., dipsticks, e.g., membranes, e.g., membrane strips described herein. In one embodiment, the kit contains a container suitable for collecting a urine sample.

A dipstick or other test device-based assay, similar to that described above, could find use in a clinical setting by quickly and reliably indicating an heightened risk for ESRD. This could save valuable time by allowing the physician to initiate treatment sooner, thereby minimizing the harmful effects of the disease.

In another embodiment, the method of the present invention may be utilized in combination with a densitometer in a device for use in a setting such as a doctor's office, a clinic or a hospital. The densitometer can provide rapid measurement of the optical density of dipstick or other test device strips that have been contacted with a bodily fluid or tissue.

Other possible approaches include the use of electrochemical sensor strips, such as those used for home glucose testing, onto which a sample is placed, and which strips include reagents for initiating a reaction when wetted by the sample. The sensor strip is inserted into a meter that measures, e.g., diffusion-limited current of a reaction species indicative of the analyte of interest, e.g., IL-8, MCP-1, IP-10, MIF, FGF-2, PDGF-AA, uPA, uPAR, or fibronectin. The meter then yields a display indicative of the concentration of analyte in the sample.

The kit can also contain a device to obtain a tissue sample, such as a cotton swab or wooden swab.

The prognostic assays described herein can be used to determine whether a subject can be administered an agent (e.g., an agent that modulates a protein described herein, e.g., a chemokine or cytokine described herein (e.g., IL-8, MCP-1, IP-10, MIF, FGF-2, or PDGF-AA), uPA, uPAR, or fibronectin) to treat a kidney disorder.

The invention is further illustrated by the following examples, which should not be construed as limiting. The contents of all references, pending patent applications and published patents, cited throughout this application are hereby expressly incorporated by reference.

EXAMPLES

Example 1

The 1$^{st}$ Joslin Study of the Natural History of Microalbuminuria: Methods

The Joslin Clinic is a referral center for patients with diabetes throughout New England. In 1991, there were about 4000 individuals with type 1 diabetes mellitus (T1DM) under the care of the Clinic. Individuals with T1DM are usually referred to the Clinic soon after diagnosis of diabetes (80% within 5 years of diagnosis) and the majority of them remain under the care of the clinic for long period of time.

In January 1991, the Microalbuminuria Laboratory was established and began screening eligible individuals. Screening was based on measurements of albumin and creatinine concentrations in random urine specimens, and the level of urinary albumin excretion was expressed as the urinary albumin to creatinine ratio (ACR, in mg/g). In 1995, the Joslin Clinic Laboratory absorbed the Microalbuminuria laboratory and subsequently provided ACR measurements for all Joslin Clinic patients. The same methods for determining concentrations of albumin and creatinine in urine were used throughout this time.

For patients attending the Joslin Clinic, the ACR is measured once a year if the preceding measurement was normal or every six months if the preceding one was elevated. This algorithm applies to all individuals with T1DM included in the study described herein. Of the approximately 20% of individuals who stopped attending the clinic, urine specimens were collected during the annual physical examination in their homes and by mailed specimen kits between examinations. About 66% of the individuals submitted urine specimens by mail when asked.

All patients with T1DM who came to the clinic between Jan. 1, 1991, and Mar. 31, 1992, were eligible to be enrolled into the 1st Joslin Study of the Natural History of Microalbuminuria. During that 15 month interval, the urine samples of every other patient were screened, i.e., 50% of the clinic population with T1DM, aged 15 to 44. Additional eligibility requirements were that the patients were Massachusetts residents and had been registered at the clinic for at least one year prior to screening. In total, 1598 patients were enrolled in the 1st Joslin Study of the Natural History of Microalbuminuria.

For the screening of each urine sample, urinalysis was performed first by the clinical lab to exclude specimens containing blood or evidence of infection. In the "eligible" urine specimens (95%), the concentrations of albumin and creatinine were determined. Urinary albumin concentration was measured by immuno-nephelometry on a BN Prospec System nephelometer (Dade Behring Inc., Newark, Del.) using the N Albumin kit (Dade Behring Diagnostics, Newark, Del.) for serum albumin and a manufacturer-supplied protocol designed specifically for the low concentration of albumin found in urine. Urine samples were centrifuged and if no albumin was detected by dipstick, the urine was tested undiluted (lower limit of detection 2 mg/ml). If the dipstick detected albumin, the urine was diluted accordingly. The coefficient of variation was <2% intra-assay, and <4% inter-assay. Urine creatinine concentration was determined by an alkaline picric colorimetric method (modified Jaffe reaction) on a SYNCHRON CX5 system (Beckman Instruments, Brea, Calif.). Coefficients of variation were <3% intra-assay and <3% inter-assay. Repeat analyses of albumin and creatinine after storage at room temperature for 72 hours gave the same results, demonstrating the feasibility of obtaining urine specimens by mail.

Measurements were expressed as the ratio of urinary concentrations of albumin in mg to creatinine in grams (ACR). Results were stored electronically and were available for patient care as well as for this research project.

All of these patients had ACR assessed in random urine specimens at each clinic visit during the subsequent 10 years. Individuals who discontinued clinic attendance or visited the clinic infrequently were supplied with mailers for submitting urine samples for ACR determinations. For analytic purposes, the 10-year period of follow-up was divided into five 2-year intervals: baseline evaluation interval and 1st through 4th follow-up intervals. Efforts were made to examine every participant with MA and a subset of those with normoalbuminuria in each of these intervals. The examinations included the following procedures:

1) Measurement of weight, height, and sitting blood pressure (measurements taken by a trained study examiner two times, 5 minutes apart after at least 10 minutes of rest);

2) Interview according to a standard questionnaire regarding cigarette smoking, past medical history, current health problems and current treatments, including prescription and non-prescription drugs (with special attention given to anti-hypertensive treatments, particularly ACE inhibitors, and recording the dates that each began and ended);

3) Blood drawing (typically 3-5 hours post meal) for biochemical measurements and DNA extraction, and collection of a random urine sample (and storage of multiple aliquots of serum, plasma and urine at −85° C. and blood for DNA at −20° C.).

Examination data were supplemented with relevant data abstracted from medical records.

Three categories of ACR were distinguished: 1) normoalbuminuria, 2) microalbuminuria (MA), and 3) overt proteinuria. Sex specific criteria to distinguish these categories were determined and published (Warram et al., *J Am Soc Neph* 7:930-37, 1996). Recently these criteria were endorsed by the National Kidney Foundation panel of experts as criteria for the diagnosis of MA in diabetes (K/DOQI clinical practice guidelines for chronic kidney disease: evaluation, classification, and stratification. Kidney Disease Outcome Quality Initiative. Am J Kidney Dis 9(2 Suppl 2): S1-246, 2002). The values of ACR were as follow: The lower limits for MA and overt proteinuria are: 17 and 250 mg of albumin/g of creatinine for men, and 25 and 355 mg/g for women. These cut points are equivalent to albumin excretion rates in timed urine collections of 30 and 300 µg/min (Warram et al., *J Am Soc Neph* 7:930-37, 1996).

The nephropathy status for each of the two-year intervals of follow-up was determined by a consensus of the available ACR measurements in the interval. For intervals with two or more ACR measurements (83%), the nephropathy status was defined by the median ACR class. Intervals with a single measurement (17%) were classified by the single value.

Glycosylated hemoglobin (HgbA1c), an aggregate index of hyperglycemia over a several-month period, was measured. Beginning in January 1995, HgbA1c was measured in the Joslin Clinical Laboratory with ion-exchange high performance liquid chromatography (Variant, Bio-Rad Laboratories, Hercules, Calif.).

In the baseline interval, the 1598 enrolled patients were distributed: 1080 normoalbuminuria, 312 MA, and 206 proteinuria or ESRD. Selected characteristics of patients in each of these groups at baseline and as of the last follow-up interval are shown in Table 1.

TABLE 1

Characteristics of individuals enrolled in the 1st Study of the Natural History of Microalbuminuria according to nephropathy status at baseline and at the last follow-up interval

| Baseline Characteristics | Normo-albuminuria | Micro-albuminuria | Proteinuria & ESRD |
|---|---|---|---|
| a. Number of patients | 1080 | 312 | 206 |
| b. Age in 1991 (y) | 29 ± 8 | 30 ± 7 | 33 ± 6 |
| c. Post-pubertal duration of diabetes (y) | 10 ± 7 | 15 ± 7 | 19 ± 5 |
| d. Years of care at Joslin | 9 ± 8 | 14 ± 9 | 17 ± 9 |
| 10 year Follow-up (Status as of the 4th follow-up interval) | | | |
| Number being followed (%) | 925 (86%) | 241 (77%) | Not followed beyond baseline, but included in genetic studies. |
| Dead (n) | 14 | 19 | |
| Living non-participants (n)* | 155 (14%) | 71 (23%) | |

*did not participate in 4th follow-up interval

Example 2

Determinants of the Onset of Microalbuminuria

The onset of MA was diagnosed if a patient with normoalbuminuria during the baseline interval developed MA or proteinuria during any of the follow-up intervals. In total, 181 such cases were identified during 6037 person-year of observation. The overall incidence rate of the onset of MA was 3.0/100 person years. It was similar among men and women and did not vary according to duration of diabetes.

Using a combination of analyses by follow-up intervals and nested case-control studies, the effects of various risk factors on the onset of MA were examined. These risk factors included hyperglycemia, cigarette smoking, parental hypertension, baseline ACR, and various candidate genes

Example 3

Determinants of Progression of Microalbuminuria to Proteinuria

Progression to proteinuria was diagnosed if a patient with normoalbuminuria or MA during the baseline interval developed proteinuria or ESRD during any of the four subsequent follow-up intervals. Out of 295 participants with MA at baseline, proteinuria developed in 41 during the 1st or 2nd follow-up interval and in 20 during the 3rd or 4th. ESRD has developed in eight of these progressors (seven on dialysis and one kidney transplant). MA developed in 109 individuals with normoalbuminuria at baseline during the 1st or 2nd follow-up interval. Proteinuria had developed in nine of them by the 4th follow-up interval, but ESRD did not develop in any. However, significant renal function loss occurred in substantial proportions of both groups (see FIG. 1).

The findings regarding the dose-response relationship between hyperglycemia and progression of microalbuminuria to proteinuria during the 1st and 2nd follow-up interval have been published (Warram et al, *Diabetes* 49:94-100, 2000). The steepest increase in risk of progression with increasing values of HgbA1c was in the range up to about 8.1% and there was no further rise in the range above 8.1%. Curiously, this was the opposite of the dose-response relationship between hyperglycemia and the onset of MA. The steepest increase in risk of onset of microalbuminuria was in the HbA1c range above 8.1%. This observation was evidence that the onset and progression of MA are governed by different processes.

The distribution of patients with MA in the baseline interval and who completed the fourth follow up is shown in Table 2. Upon completion of the fourth follow-up interval, 61 individuals had progressed from microalbuminuria to the stage of proteinuria. Life table analysis of the first occurrence of proteinuria yielded a cumulative risk of 22% after 4 intervals (8 years) of observation. This risk is much lower than the previous estimates, which were based on smaller longitudinal studies (Viberti et al., *Lancet*, 1:1430-2, 1982; Parving, et al., *Acta Endocrinol* (Copenh) 100:550-5, 1982; Mogensen and Christensen, *N Engl J Med* 311:89-93, 1984). Note that the prevalence of proteinuria in the 4th interval (Table C-2) is much less than 22%. This was because some of them progressed to ESRD, some died, and many returned to the MA stage.

TABLE 2

Nephropathy status according to intervals of follow-up in patients with MA at baseline

| NEPHROPATHY STATUS | BASELINE INTERVAL* | $1^{ST}$ FOLLOW-UP INTERVAL | $2^{ND}$ FOLLOW-UP INTERVAL | $3^{RD}$ FOLLOW-UP INTERVAL | $4^{TH}$ FOLLOW-UP INTERVAL |
|---|---|---|---|---|---|
| ESRD | — | — | 0.7% (2) | 2% (5) | 2% (6) |
| Proteinuria | — | 6% (19) | 11% (31) | 9% (28) | 8% (24) |
| Microalbuminuria | 100% (295) | 52% (154) | 44% (130) | 34% (99) | 33% (97) |
| Normoalbuminuria | — | 27% (80) | 26% (78) | 30% (88) | 32% (95) |
| Deceased | — | 0.3% (1) | 0.3% (1) | 3% (10) | 6% (19) |
| Not Followed | — | 14% (41) | 18% (53) | 22% (65) | 18% (54) |

*excludes 17 people who were lost to follow-up after baseline.
( ) number of patients A large proportion of the cohort with MA at baseline was treated with ACE inhibitors: during the 1st, 2nd, 3rd and 4th follow-up intervals. The proportion treated in the MA and proteinuria categories were 60%, 65%, 72% and 81%, respectively. The frequency of treatment with ACE inhibitors was possibly a factor contributing to the relatively low risk of progression of MA to proteinuria in this cohort.

Three determinants of MA's progression to proteinuria (despite treatment with ACE inhibitors) were identified: 1) The risk of progression to proteinuria was lower in women than men; 2) the risk of progression to proteinuria was significantly higher if diabetes duration was <15 years; and 3) the risk of progression was significantly higher if glycemic control was poor, with the dose-response relationship being similar to that described above and in Warram et al., *Diabetes* 49:94-100, 2000).

The results of the above study indicated that MA in some individuals alternately progressed and regressed, while in many others it fully remitted to normoalbuminuria. The frequency of such remissions was estimated and an effort was made to identify clinical determinants. The cohort of prevalent and new onset cases of microalbuminuria was followed for 6 years. The 6-year cumulative incidence of remission of MA to normoalbuminuria was found to be 59% (95% CI:54%-64%). Angiotensin converting enzyme (ACE) inhibitor use was not associated with MA remission, while low values of glycosylated hemoglobin, systolic blood pressure, and serum total cholesterol and triglycerides were salutary factors.

In summary, this research indicates that MA in T1DM does not imply a commitment to progressive kidney disease.

Example 4

Plasma Cystatin C Levels as Estimates of GFR/Renal Function

Plasma cystatin C level has been proposed as a good marker of GFR (Laterza et al, *Clin Chem* 48:699-707, 2002; Newman, *Cystatin C. Ann Clin Biochem* 39:89-104, 2002). It is a protein belonging to the superfamily of cysteine protease inhibitors (Newman, *Cystatin C. Ann Clin Biochem* 39:89-104, 2002). Cystatin C is a suitable marker of GFR for a number of reasons: It has low molecular weight (Mr=13,359) and is therefore freely filtered at the glomerular membrane; it is reabsorbed and catabolized by renal tubular cells; all nuclear cells produce cystatin C and at a constant rate; the production of cystatin C is not altered by inflammatory conditions, is not related to lean muscle mass, and does not have a circadian rhythm (Galteau et al., *Clin Chem Lab Med* 39:850-857, 2001); levels are not influenced by gender, age or diet; and in stored plasma, the concentration of cystatin C is stable.

Figure 2:
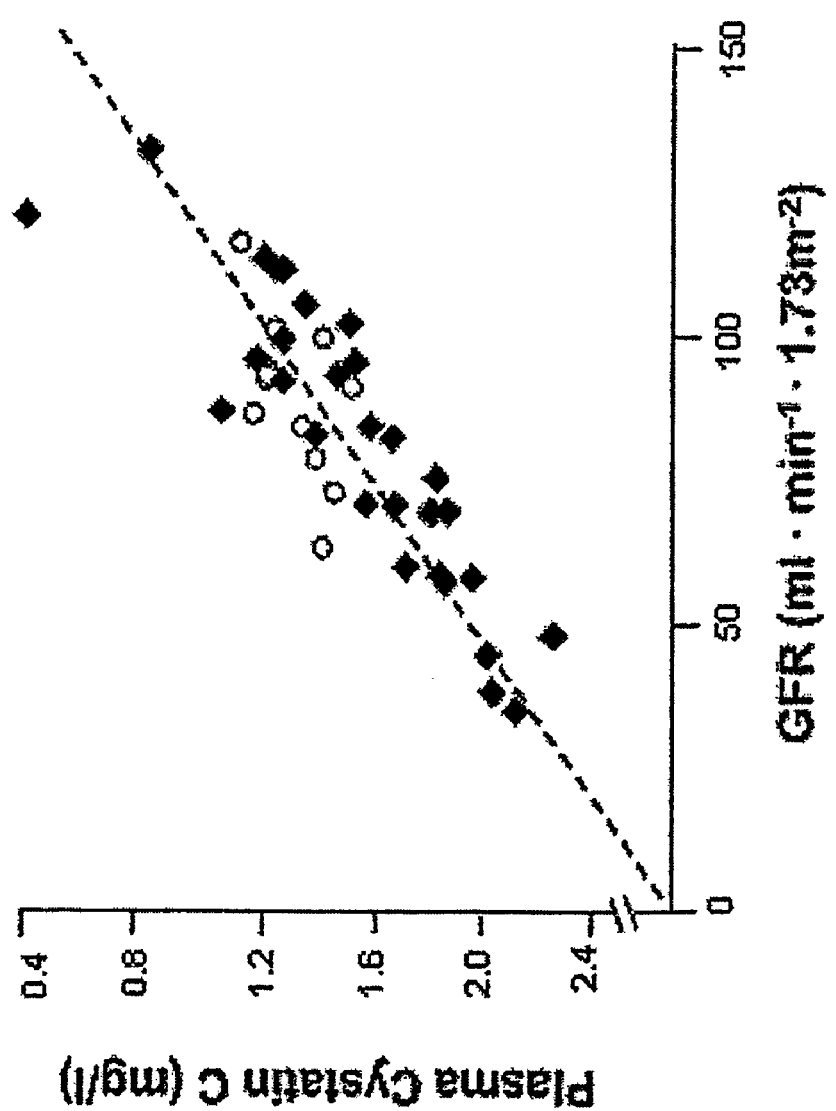
FIG. 2 is a scattergram of the reciprocal of plasma cystatin C versus iohexol clearance in patients with T1DM (black squares) and non-diabetics (white circles). GFR can be estimated by the reciprocal of cystatin C multiplied by 100.

Many studies have been conducted in which good correlation has been demonstrated between plasma or serum levels of cystatin C and GFR measured by one of the reference methods in non-diabetics and in type 2 diabetics (Kazam, et al., *Nephron* 91:13-20, 2002; Harmoinen, et al., *Clin Nephrol* 52:363-70, 1999; Mussap et al., *Kidney Int* 61:1453-61, 2002). Only recently has such a study been conducted in patients with T1DM (Tan, et al., *Diabetes Care* 25:2004-9, 2002). The relationship between plasma cystatin C and iohexol clearance (reference method for GFR) is linear in individuals with low and normal GFR values (FIG. 2). The reciprocal of plasma cystatin C (mg/l) multiplied by 100 is a valid approximation of GFR in mL/min (method adapted from Tan et al., *Diabetes Care* 25:2004-9, 2002).

In 2001, a nephelometric assay for plasma cystatin C to estimate renal function was approved by FDA for use in the U.S. In healthy individuals, the value varies from 0.51 to 0.96 mg/L. The corresponding estimates of GFR are 100/0.51=196 ml/min. and 100/0.96=104 ml/min.

Figure 3:
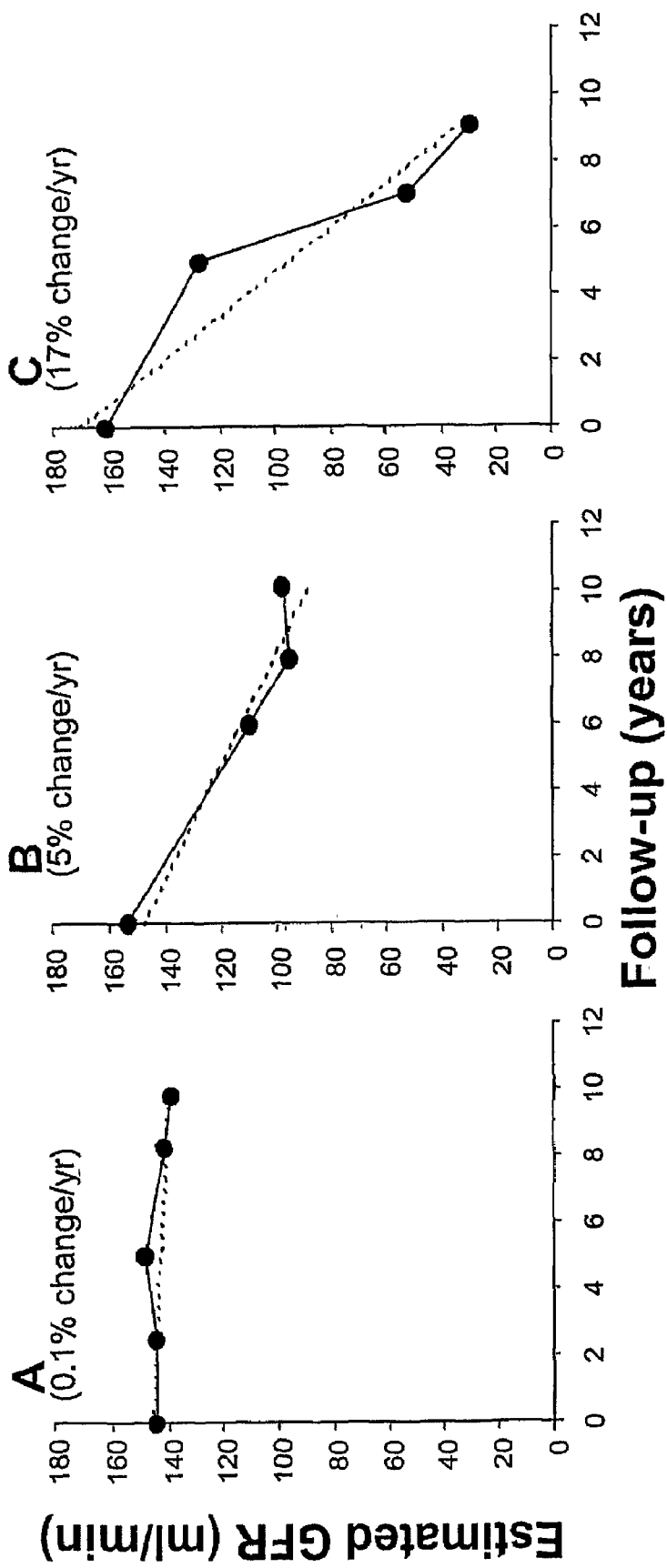
FIG. 3 is a set of graphs representing the estimated GFR (based on plasma cystatin C) plotted over time for three individuals with MA.

Cystatin C is measured in plasma by an immunoassay based on rabbit monospecific anti-human cystatin C antiserum (Dade Behring Diagnostics, Newark, Del.) with a BN Prospec System nephelometer (Dade Behring Inc., Newark, Del.). This method was used beginning at the end of 2001 to determine plasma cystatin C levels of patients studied in the 1st Joslin Study of the Natural History of Microalbuminuria. The results are summarized in FIGS. 1 and 3. The assay coefficient of variation is 3.4% for values in the range 0.5 to 2 mg/dl with a detection threshold 0.3 mg/dl. Freezing and thawing and storage at −85° C. did not have an impact on measured levels of plasma cystatin C. Identical values were obtained in plasma and in serum.

Example 5

Renal Function Loss in Individuals with T1DM

Three groups of individuals were examined to investigate changes in renal function in T1DM: 1) those with normoalbuminuria during 10-year follow-up, 2) those with onset of MA during follow-up, and 3) those with MA at baseline. The number of patients in each group was determined by the availability of at least three stored plasma specimens spanning the follow-up.

Estimated renal function in the three groups at baseline is shown at the top of FIG. 1. Mean baseline GFR in the group of patients who later developed MA was the same as that for the group who remained with normoalbuminuria, while mean baseline GFR was significantly lower in those who already had MA (p<0.001). The rate of change in GFR in each individual during follow-up was estimated by linear regression and expressed as percent change per year. The results for the three study groups are plotted in FIG. 1. The group with normoalbuminuria had only small changes in renal function. However, the group with the onset of MA during follow-up and the group with MA at baseline were not different from each other, but they both experienced significant loss of renal function in comparison with individuals with normoalbuminuria (p<0.001).

With a rate of decline of 5% per year (horizontal dotted line), a patient with a GFR of 150 ml/min would reach end stage renal disease (GFR 25 ml/min) in 35 years. Thus, this rate of decline can be considered clinically significant. In the group of individuals with MA, the rate of decline was ≧5% per year for 25% (95% CI: Cooper, et al., *Metabolism* 47:3-6, 1998; Banba, et al.; *Kidney Int* 58:684-90, 2000) of the group. The finding that a significant proportion of individuals with MA began losing renal function soon after the onset of MA was unexpected. This was not recognized previously because of the assumption that declining renal function began much later during the course of diabetic nephropathy.

Example 6

Determinants of Renal Function Loss in Patients with T1DM and Microalbuminuria

To investigate possible determinants of early renal function loss, individuals with T1DM and MA were divided according to whether the rate of renal function loss was above or below the mean for patients with MA (≧3% per year, decliners; <3% per year, non-decliners). As the findings were similar in onset and prevalent cases of MA, these cases were combined. Clinical characteristics of the two subgroups are shown in Table 3 (data are mean±SD).

TABLE 3

Clinical characteristics of individuals with T1DM and microalbuminuria according to whether renal function declined during follow-up

| | Renal function in individuals with Microalbuminuria | | |
| --- | --- | --- | --- |
| Characteristic | Non-declining N = 78 | Declining N = 44 | p-value |
| Age at baseline* | 31.0 ± 7.1 | 32.7 ± 7.8 | 0.22 |
| % Post-Pubertal Duration at baseline <15 years | 46% | 57% | 0.26 |
| Cystatin C at baseline* | 0.70 ± 0.13 | 0.65 ± 0.13 | 0.12 |
| Mean arterial pressure at baseline* | 91.7 ± 8.6 | 91.5 ± 9.4 | 0.92 |
| Mean arterial pressure at 1st interval | 91.4 ± 9.0 | 92.3 ± 10.4 | 0.64 |
| Mean arterial pressure at 2nd interval | 91.9 ± 9.3 | 95.1 ± 10.8 | 0.16 |
| % on ACEI Rx in baseline interval* | 22% | 23% | 0.89 |
| % on ACEI Rx in 1st interval | 37% | 40% | 0.75 |
| % on ACEI Rx in 2nd interval | 48% | 50% | 0.85 |
| HbA1c at baseline* | 9.0 ± 1.4 | 9.7 ± 1.5 | 0.02 |
| HbA1c in 1st interval | 8.9 ± 1.3 | 9.6 ± 1.4 | 0.008 |
| HbA1c in 2nd interval | 8.8 ± 1.4 | 9.2 ± 1.4 | 0.14 |
| Cholesterol at baseline* | 199.8 ± 41.4 | 215.7 ± 41.0 | 0.06 |
| Cholesterol in 1st interval | 191.7 ± 33.7 | 199.9 ± 43.0 | 0.27 |
| Cholesterol in 2nd interval | 191.3 ± 31.6 | 209.6 ± 40.8 | 0.01 |
| Triglycerides at baseline*† | 106.8 (76.140) | 124.3 (96.151) | 0.19 |
| Triglycerides in 1st interval† | 96.3 (67.124) | 112.8 (72.152) | 0.23 |
| Triglycerides in 2nd interval† | 95.9 (64.136) | 104.2 (65.151) | 0.53 |
| ACR at baseline*† | 43.5 (26.68) | 47.8 (23.97) | 0.53 |
| ACR in 1st interval† | 26.5 (10.63) | 46.6 (17.150) | 0.04 |
| ACR in 2nd interval† | 23.6 (8.70) | 98.3 (19.321) | 0.001 |
| ACR in 3rd interval† | 21.7 (8.43) | 122.8 (13.1125) | 0.001 |

TABLE 3-continued

Clinical characteristics of individuals with
T1DM and microalbuminuria according to whether
renal function declined during follow-up

| | Renal function in individuals with Microalbuminuria | | |
|---|---|---|---|
| Characteristic | Non-declining N = 78 | Declining N = 44 | p-value |

*For individuals with new onset MA baseline is the interval in which they developed MA, whereas for individuals with prevalent MA baseline is the interval in which they enrolled in the study.
†Data are geometric means and interquartile range.

Patients with T1DM and MA with a renal function loss of 3% or more per year (decliners) did not differ from non-decliners with regard to age, duration of diabetes, level of baseline plasma cystatin C, blood pressure, or treatment with ACE inhibitors. However, decliners differed from non-decliners with regard to level of HbA1c, serum cholesterol, and triglycerides, although for the last the evidence was weak.

Interestingly, decliners and non-decliners had similar ACR values in the low MA range at baseline. The levels of ACR actually increased with follow-up time among decliners and decreased in the non-decliners. The differences were highly significant.

Example 7

Urinary Chemokines and Renal Function Loss in T1DM

Research has indicated a significant correlation between damage to renal tubules and interstitium, and loss of renal function in various kidney diseases. To determine whether this was also true of patients with T1DM and MA, urine levels of MCP-1 and IL-8 were measured. MCP-1 and IL-8 are two chemokines that have been consistently associated with tubular and interstitial damage in cellular and animal studies. The current study was done in the subset of the individuals shown in Table 3 who had a stored urine specimen available. For the majority, the available urine specimen was collected during the 1st follow-up (see Table 3 above). As the findings were similar in onset and prevalent cases of MA, these groups were combined and shown in Table 4 according to whether renal function was declining or not. For comparison, urine values of these chemokines are shown for patients with T1DM and normoalbuminuria for the 10 years of follow-up.

TABLE 4

Urine values of two chemokines considered to be markers of damage
to renal tubules and interstitium according to study group

| | Normo- albuminurics N = 30 | Renal function in Microalbuminurics | | |
|---|---|---|---|---|
| Chemokines | | Non-declining N = 47 | Declining N = 30 | p-value* |
| Concentrations (pg/ml)†: | | | | |
| MCP-1 | 118 ± 152 | 139 ± 135 | 225 ± 170 | 0.01 |
| IL-8 | 31 ± 63 | 13 ± 16 | 61 ± 106 | 0.02 |
| Concentrations adjusted for urine creatinine (pg/mg)†: | | | | |
| MCP-1 | 1.35 ± 1.26 | 1.65 ± 1.25 | 3.21 ± 3.31 | 0.006 |
| IL-8 | 0.41 ± 0.79 | 0.17 ± 0.19 | 0.69 ± 0.90 | 0.02 |

*Data were transformed to the log scale for significance testing. P-value for comparison of non-declining versus declining.
†Concentrations of the chemokines were determined by using the Quantikine immunoassay kit (R&D Systems, Minneapolis, MN). Data are mean ± standard deviation.

Patients with declining renal function had significantly elevated urinary levels of MCP-1 and IL-8 in comparison with the two other groups. In a general linear model, these associations remained statistically significant (p<0.01) when other risk factors such as HbA1c, ACR, duration of diabetes, and serum lipids were included. In contrast, plasma levels of these chemokines did not differ among the study groups.

Example 8

Use of MultiAnalyte Profiling Kit to Measure Multiple Cytokines and Chemokines in a Single Urine Sample The MultiAnalyte Profiling Kit (R&D Systems, Minneapolis, Minn.) can measure multiple cytokines and chemokines in a single urine sample. This multiplex assay uses Luminex™×MAP™ detection technology (Luminex Corporation, Austin, Tex.). Luminex™×MAP™ latex microbeads are dyed with two fluorophores. Precise ratios of the fluorophores create distinguishable beads sets. These beads are the solid phase for the multiplex immunoassay.

The Luminex™×MAP™ functions as follows. Antibodies to capture a chemokine or cytokine are coupled to specific bead sets. Each unique antibody-coated bead set is then an "individual chemokine or cytokine immunoassay." Various antibody-coated bead sets can be mixed together (i.e., multiplexed) and incubated with a urine sample. After chemokines or cytokines bind to bead sets coated with their corresponding capture-antibodies, a phycoerythrin (PE)-conjugated specific detection antibody is used as the reporter. The amount of chemokine/cytokine bound is proportional to the PE signal generated by each bead set. The fluorescence levels generated by the beads and the PE-labeled antibody are analyzed on a Luminex platform using a dual laser system. Real time quantitative data are generated for each chemokine or cytokine.

A custom designed MultiAnalyte Profiling Kit was produced and included the chemokines MCP-1, IL-8, and IP-10, and the cytokines TNF-alpha, IL-1beta, and IL-6. The test urines were from 18 individuals, 9 with declining renal function and 9 with non-declining renal function. Means and CVs (range 7-12%) with the multiplexing technology were similar to the single immunoassay technology.

Urinary chemokines can be increased by elevated levels of pro-inflammatory cytokines such as TNF-alpha, IL-1B, and IL-6, either in serum or in kidney, the latter being excreted into the urine (Oberholzer et al, *Crit Care Med.* 28(suppl.): N3-N12, 2000; Esch and Stefano, *Med Sci Monit* 8:1-9, 2002; Prodjosudjadi et al., *Kidney Int* 48:1477-1486, 1995; Vesey et al., *Kidney Int* 62:31-40, 2002. In a pilot study of 34 MA individuals (17 with declining renal function and 17 non-decliners), urinary MCP-1 and IP-10 were correlated with pro-inflammatory cytokines, whereas IL-8 was not correlated with any of them. Urinary levels of MCP-1, IL-8 and IP-10 were all elevated in decliners in comparison with non-decliners. Among cases with declining renal function, there was moderate correlation between urinary levels of MCP-1 and the other two chemokines (Table 5) but not in those without declining renal function. These findings indicate that tubular damage associated with declining renal function is manifested by an increase in urinary levels of several chemokines that are only moderately correlated with each other.

TABLE 5

Pearson correlation coefficients between pairs of the three chemokines in patients with T1DM and MA according to presence of declining renal function (cases) or absence of declining renal function (controls).

| | DECLINERS (n = 9) | | NON-DECLINERS (n = 9) | |
| --- | --- | --- | --- | --- |
| | IL-8 | IP-10 | IL-8 | IP-10 |
| MCP-1 | 0.53 | 0.41 | 0.02 | −0.10 |
| IL-8 | | 0.16 | | 0.37 |

The data are cross-sectional. The time-courses for the elevations of each chemokine may not be synchronous. While the earliest available archived urine sample for each of the 18 individuals was selected for testing, the sampling times varied with respect to the onset of MA.

We claim:

1. A method of evaluating a subject for risk or predisposition of reduced renal function over time, the method comprising:
   (a) identifying a subject having normoalbuminuria or microalbuminuria;
   (b) evaluating the level interferon inducible protein-10 (IP-10); and
   (c) correlating an aberrant level IP-10 with risk or predisposition of reduced renal function over time, wherein an elevated level of IP-10 is correlated with an increased risk or predisposition of reduced renal function over time.

2. The method of claim 1, wherein the subject has normal kidney function as evaluated by one or more of: glomerular filtration rate (GFR), urine protein level, blood creatinine level, urine creatinine level, creatinine clearance, and blood urea nitrogen.

3. The method of claim 1, wherein the level is detected using a dipstick assay.

4. The method of claim 1, wherein the subject has or is at risk for diabetic nephropathy.

5. The method of claim 1, wherein the subject has or is at risk for end stage renal disease (ESRD).

6. The method of claim 1, wherein the subject has or is at risk for diabetes.

7. The method of claim 6, wherein the subject has or is at risk for type 1 diabetes.

8. The method of claim 6, wherein the subject has or is at risk for type 2 diabetes.

9. The method of claim 1, wherein the level of interferon inducible protein-10 (IP-10) is evaluated in a urinary sample of the subject.

10. The method of claim 1, wherein the subject has normoalbuminuria.

11. The method of claim 1, wherein the subject has microalbuminuria.

12. The method of claim 1, wherein the evaluating step comprises performing one or more of: enzyme-linked immunoassay, radioimmunoassay, immunoblot assay, in situ hybridization, Northern blot analysis, Western blot analysis, and bead-based immunoassay.

13. The method of claim 1, further comprising comparing the level of IP-10 to a reference profile or a baseline value of IP-10.

14. A method of evaluating a subject for risk or predisposition of reduced renal function over time, the method comprising: identifying a subject at risk for, or having, diabetes, wherein the subject has normoalbuminuria or microalbuminuria, and evaluating a level of interferon inducible protein-10 (IP-10) in a urinary sample of the subject, wherein an elevated level of IP-10 indicates increased risk or predisposition of reduced renal function over time.

15. The method of claim 14, wherein the level is detected using a dipstick assay.

16. The method of claim 14, further comprising comparing the level of IP-10 to a reference profile or a baseline value of IP-10.

* * * * *